(12) United States Patent
Chiu et al.

(10) Patent No.: US 7,470,711 B2
(45) Date of Patent: Dec. 30, 2008

(54) PIPERIDINYL SUBSTITUTED CYCLOHEXANE-1,4-DIAMINES

(75) Inventors: George Chiu, Bridgewater, NJ (US); Shengjian Li, Belle Mead, NJ (US); Peter J. Connolly, New Providence, NJ (US); Virginia L. Pulito, Flemington, NJ (US); Jingchun Liu, Three Bridges, NJ (US); Steven A. Middleton, Flemington, NJ (US)

(73) Assignee: Janssen Pharmaceutica N.V. (BE)

( * ) Notice: Subject to any disclaimer, the term of this patent is extended or adjusted under 35 U.S.C. 154(b) by 283 days.

(21) Appl. No.: 11/376,348

(22) Filed: Mar. 15, 2006

(65) Prior Publication Data

US 2006/0217419 A1   Sep. 28, 2006

Related U.S. Application Data

(60) Provisional application No. 60/664,302, filed on Mar. 22, 2005.

(51) Int. Cl.
*A61K 31/451* (2006.01)
*A61K 31/453* (2006.01)
*C07D 211/22* (2006.01)
*C07D 405/12* (2006.01)

(52) U.S. Cl. .................. 514/321; 514/331; 546/196; 546/232

(58) Field of Classification Search .................. None
See application file for complete search history.

(56) References Cited

U.S. PATENT DOCUMENTS 5,569,659 A   10/1996 Reitz

FOREIGN PATENT DOCUMENTS

EP         121972    10/1984
WO      03/048118   * 6/2003

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Testa et al. Pure Appl. Chem. vol. 76, pp. 907-914 (2004).*
Vippagunta et al Advanced Drug Delivery Reviews, vol. 48, pp. 3-26 (2001).*
Harrison et al., "Molecular characterization of $\alpha_1$- and $\alpha_2$ adrenoceptors", Trends Pharmacol Sci; 1991; 62-67.
Morrow and Creese, "Characterization of $\alpha_1$-Adrenergic Receptor Subtypes in Rat Brain: A Reevaluation of [$^3$H] WB4104 and [$^3$H] Prazosin Binding", Mol. Pharmacol; 1986; 29:321-330.
Minneman et al., "Comparison of $\alpha_1$-Adrenergic Receptor Subtypes Distinguished by Chlorethylclonidine and WB 4101", Mol. Pharmacol; 1988; 33:509-514.

Schwinn et al., "Molecular Cloning and Expression of the cDNA for a Novel $\alpha_1$-Adrenergic Receptor Subtype", J.Biol Chem; 1990; 265: 8183-8189.
Ramaro et al., "Genomic Organization and Expression of the Human $\alpha_{1B}$-Adrenergic Receptor", J Biol Chem; 1992; 267:21936-21945.
Bruno et al., "Molecular Cloning and Sequencing of a cDNA Encoding a Human $\alpha_{1A}$-Adrenergic Receptor", Biochem Biophys Res Commun; 1991; 179: 1485-1490.
Goetz et al., "BMY 7378 is a selective antagonist of the D subtype of $\alpha_1$-adrenoceptors", Eur J Pharmacol; 1995; 272:R5-R6.
Caine, "The present role of alpha-adrenergic blockers in the treatment of benign prostatic hypertrophy", J Urol; 1986; 136: 1-4.
Lepor, "Localization of the $\alpha_{1A}$-adrenoceptor in the human prostate", J. Urol. 1995, 154, 2096-2099.
Perlberg et al., "Adrenergic Response of Bladder Muscle in Prostatic Obstruction," Urology; 1982; 20:524-527.
Restorick and Mundy, "The density of cholinergic and alpha and beta adrenergic receptors in the normal and hyper-reflexic human detrusor", Br J Urol; 1989; 63: 32-35.
Smith and Chapple, "In Vitro Response of Human Bladder Smooth Muscle in Unstable Obstructed Male Bladders: A Study of Pathophysiological Causes," Neurolog Urodyn; 1994; 12: 414-415.
Walden et al., "Localization of mRNA and receptor binding sites for the $\alpha_{1A}$-adrenoceptor subtype in the rat, monkey and human urinary bladder and prostate", J Urol; 1997; 157: 1032-1038.
Malloy et al., "$\alpha_1$-Adrenoceptor Receptor Subtypes in Human Detrusor", J Urol; 1998; 160: 937-943.
Piascik and Perez, "$\alpha_1$-Adrenergic Receptors: New Insights and Directions", J Pharmacol Exp Ther; 2001; 298: 403-410.

(Continued)

*Primary Examiner*—Emily Bernhardt

(57) ABSTRACT

The present invention relates to piperidine substituted cyclohexane-1,4-diamine compounds of Formula (I)

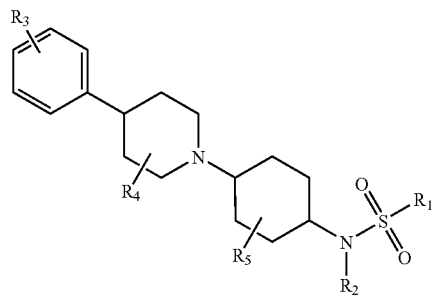

and pharmaceutically acceptable forms thereof, as $\alpha_{1d}/\alpha_{1d}$ adrenoreceptor modulators for the treatment of benign prostatic hypertrophy and lower urinary tract symptoms. The present invention also relates to pharmaceutical compositions comprising said new compounds, new processes to prepare these new compounds and new uses as a medicine as well as method of treatments.

7 Claims, No Drawings

OTHER PUBLICATIONS

Danuser and Thor, "Inhibition of central sympathetic and somatic outflow to the lower urinary tract of the cat by the $\alpha_1$-adrenergic receptor antagonist prazosin", J Urol; 1995; 153: 1308-1312.

Ramage and Wyllie, "A comparison of the effects of doxazosin and terazosin on the spontaneous sympathetic drive to the bladder and related organs in anaesthetized cats", Eur J Pharmacol; 1995; 294: 645-650.

Ishizuka et al., "Micturition in conscious rats with and without bladder outlet obstruction: role of spinal $\alpha_1$-adrenoceptors", Br J Pharmacol; 1996; 117:962-966.

Persson et al., "Spinal and peripheral mechanisms contributing to hyperactive voiding in spontaneously hypertensive rats", Am J Physiol; 1998; 275:R1366-1373.

Steers et al., "The spontaneously hypertensive rat: insight into the pathogenesis of irritative symptoms in benign prostatic hyperplasia and young anxious males", 1999; Exp Physiol, 1999; 84:137-147.

Smith et al., $\alpha_1$-Adrenergic receptors in human spinal cord: specific localized expression of mRNA encoding "$\alpha_1$-adrenergic receptor subtypes at four distinct levels", Mol Brain Res; 1999; 63:254-261.

Abrams et al. "Tamsulosin, a selective $\alpha_{1C}$-adrenoceptor antagonist: a randomized, controlled trial in patients with benign prostatic 'obstruction' (symptomatic BPH)", Br J Urol; 1995; 76:325-336.

Lepor, "Phase III multicenter placebo-controlled study of tamsulosin in benign prostatic hyperplasia", Urology; 1998; 51:892-900.

Rudner et al., "Subtype Specific Regulation of Human Vascular $\alpha_1$-Adrenergic Receptors by Vessel Bed and Age", Circulation; 1999; 100:2336-2343.

Lepor, "Long-term evaluation of tamsulosin in benign prostatic hyperplasia: placebo-controlled, double-blind extension of phase III trial", Urology; 1998; 51:901-906.

Heaton, "The serious side of lifestyles issues in urology", Brit J Urol Int; 2003; 92:875-879.

Habashita, et al. "Preparation of Nitrogen-Containing Heterocyclic Compounds as CXCR4 Regulators' Abstract". Database CASPLUS on STN (Columbus, OH, USA), No. 141:71555. (2004).

International Search Report, PCT/US06/09192, Sep. 12, 2006.

Harrison et al., "Molecular characterization of $\alpha_1$- and $\alpha_2$ adrenoceptors", Trends Pharmacol Sci; 1991; 62-67.

Morrow and Creese, "Characterization of $\alpha_1$ Adrenergic receptor Subtypes in Rat Brain: A Reevaluation of [$^3$H] WB4104 and [$^3$H] Prazosin Binding", Mol. Pharmacol; 1986; 29:3201-330.

Minneman et al., "Comparison of $\alpha_1$-Adrenergic Receptor Subtypes Distinguished by Chlorethylclonidine and WB 4101", Mol. Pharmacol; 1998; 33:509-514.

Schwinn et al., "Molecular Cloning and Expression of the cDNA for a Novel $\alpha_1$-Adrenergic Receptor Subtype", J.Biol Chem; 1990; 265: 8183-8189.

Ramarao et al., "Genomic Organization and Expression of the Human $\alpha_{1B}$-Adrenergic Receptor", J Biol Chem; 1992; 267:21936-21945.

Bruno et al., "Molecular Cloning and Sequencing of a cDNA Encoding a Human $\alpha_{1A}$-Adrenergic Receptor", Biochem Biophys Res Commun; 1991; 179: 1485-1490.

Goetz et al., "BMY 7378 is a selective antagonist of the D subtype of $\alpha_1$-adrenoceptors", Eur J Pharmacol; 1995; 272:R5-R6.

Caine, "The present role of alpha-adrenergic blockers in the treatment of benign prostatic hypertrophy", J Urol; 1986; 136: 1-4.

* cited by examiner

PIPERIDINYL SUBSTITUTED CYCLOHEXANE-1,4-DIAMINES

CROSS REFERENCE TO RELATED APPLICATIONS

This present application claims benefit of U.S. Provisional Patent Application Ser. No. 60/664,302, filed Mar. 22, 2005, which is incorporated herein by reference in its entirety and for all purposes.

FIELD OF THE INVENTION

The present invention relates to new compounds, more particularly new piperidine substituted cyclohexane-1,4-diamines as selective $\alpha_{1a}/\alpha_{1d}$ adrenoreceptor modulators for the treatment of benign prostatic hypertrophy and/or lower urinary tract symptoms. The present invention also relates to pharmaceutical compositions comprising said new compounds, new processes to prepare these new compounds, to the use of these compounds as $\alpha_{1a}/\alpha_{1d}$ adrenoreceptor modulators and new uses as a medicine as well as method of treatments.

RELATED ART

The adrenergic receptors (ARs), through which norepinephrine and epinephrine exert their biological activities, are targets for many therapeutically important drugs. The $\alpha_1$-ARs play a dominant role in control of smooth muscle contraction and are important in control of blood pressure, nasal congestion, prostate function, and other processes (Harrison et al., Trends Pharmacol Sci; 1991; 62-67). The $\alpha_1$-ARs were originally classified by pharmacological profiling into two subtypes, $\alpha_{1a}$ and $\alpha_{1b}$ (Morrow and Creese, Mol. Pharmacol; 1986; 29: 231-330; Minneman et al., Mol. Pharmacol; 1988; 33:509-514). Three genes encoding different $\alpha_1$-AR subtypes ($\alpha_{1a}$, $\alpha_{1b}$, and $\alpha_{1d}$) have been cloned for a number of species, including human (Schwinn et al., J. Biol Chem; 1990; 265: 8183-8189; Ramarao et al., J Biol Chem; 1992; 267:21936-21945; Bruno et al., Biochem Biophys Res Commun; 1991; 179: 1485-1490). These three cloned $\alpha_1$-ARs are best differentiated from one another on the basis of the relative binding affinities of a series of antagonist compounds. There is general agreement that the $\alpha_{1a}$- and $\alpha_{1b}$-ARs correspond to the pharmacologically defined $\alpha_{1a}$- and $\alpha_{1b}$-ARs, while the functional role of the $\alpha_{1d}$-AR is less clear, although it appears to mediate contraction of certain blood vessels (Goetz et al., Eur J Pharmacol; 1991; 272:R5-R6). Like other ARs, the $\alpha_1$-ARs are members of the G-protein coupled receptor super family, and in most cells the primary functional response to activation of all $\alpha_1$-AR subtypes is an increase in intracellular $Ca^{2+}$.

Benign prostatic hyperplasia (BPH) is a non-malignant enlargement of the prostate and is the cause of lower urinary tract symptoms (LUTS) in a large segment of the elderly male population. Symptoms such as straining, hesitancy, dribbling, weak stream, and incomplete emptying are classified as voiding or obstructive symptoms. Obstructive symptoms are primarily due to pressure upon the urethra from the physical mass of the enlarged prostate gland (the static component) and the increased tone of the smooth muscle of the prostate stroma and bladder neck (the dynamic component) (Caine, J Urol; 1986; 136: 14). Irritative or storage symptoms associated with BPH are frequency, urgency, nocturia, dysuria, and burning sensation. Patients feel that these symptoms are more disturbing than the obstructive symptoms. As the urine flow is reduced, due to the bladder outlet obstruction, the wall around the bladder base thickens and becomes hyperactive.

Functional studies have established that prostate smooth muscle tone is maintained through $\alpha_1$-ARs and that these receptors mediate the dynamic component of obstruction. $\alpha_1$-AR antagonists have successfully been used to treat the obstructive symptoms associated with BPH (Jardin et al., Scientific Communications Int; 1998; pp 559-632). Furthermore, the $\alpha_{1a}$-AR subtype comprises the majority of $\alpha_1$-ARs in human prostatic smooth muscle and has been shown to mediate contraction in this tissue. Originally introduced as antihypertensive agents, $\alpha_1$-AR antagonists have become increasingly important in the management of BPH. $\alpha_1$-AR antagonists reduce smooth muscle tone in the prostate and lower urinary tract, thereby relaxing the bladder outlet and increasing urinary flow. The major disadvantage of non-selective $\alpha_1$-blockers is their adverse effect profile, particularly vasodilatation leading to dizziness, postural hypotension, asthenia, and occasionally syncope. For this reason, it would be desirable to block $\alpha_1$-ARs in the lower urinary tract without antagonizing the $\alpha_1$-ARs responsible for maintaining vascular tone.

A number of factors can be involved in lower urinary tract symptoms. Adrenergic stimulation of the bladder results in relaxation due to $\beta$-ARs, which dominate over contraction-mediating $\alpha_1$-ARs. Bladder contraction is primarily mediated by muscarinic receptors. Some studies indicate that the contribution from $\alpha_1$-ARs increases in hyperactive bladders due to bladder outlet obstruction or other conditions (Perlberg et al., Urology; 1982; 20:524-527); Restorick and Mundy, Br J Urol; 1989; 63: 32-35). However another study finds no change in $\alpha_1$-AR receptor function between normal and hypertrophic bladder due to outlet obstruction (Smith and Chapple, Neurolog Urodyn; 1994; 12: 414-415). It remains unclear, which $\alpha_1$-AR is dominant in the human bladder. One study reported a predominance of the $\alpha_{1a}$ subtype mRNA in the bladder dome, base, and trigone (Walden et al., J Urol; 1997; 157: 414-415). Another report found that the $\alpha_{1d}$ subtype is present as 66% of the $\alpha_1$-ARs at both the mRNA and protein levels, while the $\alpha_{1a}$ subtype is present as 34% of the total, with no evidence of the $\alpha_{1b}$ subtype (Malloy et al., J Urol; 1998; 160: 937-943). Drugs that selectively antagonize only the $\alpha_{1a}$-AR subtype appear to have little effect upon the irritative symptoms of BPH. Ro-70004, a $\alpha_{1a}$ subtype-selective compound was reported to be discontinued in clinical studies when it was found to have poor efficacy in treating these symptoms (Blue et al., Abstract 5$^{th}$ International Consultation on BPH (June 25-28) 2000). $\alpha_{1d}$-ARs may be involved in mediating the irritative symptoms; however, the location of these $\alpha_{1d}$-ARs is unknown (Piascik and Perez, J Pharmacol Exp Ther; 2001; 298: 403-410).

Studies have demonstrated Central Nervous Systems (CNS) inhibitory effects of $\alpha_1$ antagonists upon the sympathetic and somatic outflow to the bladder in cats (Danuser and Thor, J Urol; 1995; 153: 1308-1312; Ramage and Wyllie, Eur J Pharmacol; 1995; 294: 645-650). Intrathecally administered doxazosin caused a decrease in micturition pressure in both normal rats and rats with bladder hypertrophy secondary to outlet obstruction (Ishizuka et al., Br J Pharmacol; 1996; 117:962-966). These effects may be due to a reduction in parasympathetic nerve activity in the spinal cord and ganglia. Other studies used spontaneously hypertensive rats, which have overactive bladders, to demonstrate that $\alpha_1$-AR antagonism only given intrathecally caused a return to normal micturition (Persson et al., Am J Physiol; 1998; 275:R1366-1373, Steers et al. 1999; Exp Physiol; 84:137-147.). Antagonists administered intra-arterially near the bladder, or ablation of peripheral noradrenergic nerves, had no effect upon the bladder overactivity in these animals, indicating that $\alpha_1$-ARs in the spinal cord control the bladder activity. Spinal $\alpha_1$-ARs may be important targets for pharmacological treatment of BPH symptoms in humans as well. All three $\alpha_1$-AR subtype mRNAs are found throughout the human spinal cord, however the $\alpha_{1d}$ subtype mRNA is present at twice the level of the other subtypes, particularly in the ventral sacral motor neurons and autonomic parasympathetic pathways. (Stafford-Smith et al., Mol Brain Res; 1998; 63:234-261). There may be clinical advantages to the pharmacological blockade of the $\alpha_{1d}$-ARs in the CNS in reducing BPH symptoms.

Antagonism of $\alpha_{1d}$-ARs in the CNS and bladder may be an important activity in reducing the irritative or filling symptoms of BPH and improving patient symptom scores. Tamsulosin (Flomax®, Yamanuchi and Boehringer Ingelheim) is a $\alpha_1$-AR antagonist, which is about 15-fold selective for the $\alpha_{1a}$ and $\alpha_{1d}$ subtypes over the $\alpha_{1b}$ subtype. Large clinical trials of BPH patients with tamsulosin showed improvement in both obstructive and irritative symptoms, however, cardiovascular and erectile dysfunction side effects were seen (Abrams et al. Br J Urol; 1995; 76:325-336; Chapple et al., Eur Urol; 1996; 29:155-167; Lepor, Urology; 1998; 51:892-900). Patients treated with non-selective $\alpha_1$ antagonists also have improvement in both obstructive and irritative symptoms, although the risk of vascular side effects is greater. Generally, the $\alpha_{1a}$ subtype predominates in arteries at the mRNA and protein levels, while all three subtypes are found in veins. The particular vessel bed is important in that the $\alpha_{1a}$ is the subtype found primarily in the splanchnic and coronary arteries, while the $\alpha_{1d}$ subtype is the predominant subtype found in the aorta. The $\alpha_1$-AR subtypes in the vasculature have been found to change with age. Contraction of the mammary artery is mediated by both $\alpha_{1a}$ and $\alpha_{1b}$ subtypes. The number of $\alpha_1$ receptors in the mammary artery doubles with age; however, the $\alpha_{1b}$ subtype increases to a greater extent than the $\alpha_{1a}$ subtype (Raudner et al., Circulation; 1999; 100: 2336-2343). The $\alpha_{1b}$ subtype may play a greater role in vascular tone in elderly patients. This suggests that an $\alpha_{1a}$ and $\alpha_{1D}$-selective antagonist may have less effects upon the vasculature in elderly BPH patients, resulting in fewer cardiovascular side effects than are seen with non-selective $\alpha_1$ antagonists, but provide relief from both obstructive and irritative symptoms.

A uroselective, cardiovascular-sparing $\alpha_1$-AR antagonist would be expected to provide symptomatic relief of BPH comparable to currently marketed non-selective agents such as terazosin/Hytrin®, doxazosin/Cardura®, alfuzosin/Xatral®/Uroxatral® and weakly selective tamsulosin/Flomax®/Harnal®, without the undesirable side effects of postural hypotension, dizziness, and syncope. Ejaculatory dysfunction, or retrograde ejaculation, is a side effect seen in 10 to 35% of patients using tamsulosin (Lepor, Urology; 1998; 51:901-906; Andersson and Wyllie, Brit J Urol Int; 2003; 92:876-877). This activity has been attributed to tamsulosin antagonism at the 5-HT$_{1a}$ receptor. This often leads to discontinuation of treatment. Furthermore, the non-selective $\alpha_1$-AR antagonists and tamsulosin are contraindicated for use in conjunction with PDE inhibitors. There is likely to be high co-morbidity between LUTS and erectile dysfunction patients. Patients being treated for LUTS with the current $\alpha_1$-AR blockers will find that they are excluded from using PDE inhibitors. An $\alpha_1$-AR antagonist with a receptor subtype binding profile, which is selective for the $\alpha_{1a}$ and $\alpha_{1d}$, subtypes, but with relatively little antagonism of the $\alpha_{1b}$ subtype may effectively treat both obstructive and irritative symptoms of BPH. Such a compound is likely to have a low cardiovascular side effect profile and allow for use in conjunction with PDE inhibitors. Also low binding activity at the 5-HT$_{1a}$ receptor is likely to reduce the incidence of ejaculatory side effects.

LUTS also develop in women of a certain age. As in men, LUTS in women include both filling symptoms such as urgency, incontinence and nocturnia, and voiding symptoms such as weak stream, hesitancy, incomplete bladder emptying and abdominal straining. The presence of this condition both in men and women suggests that at least part of the aetiology may be similar in the two sexes.

Accordingly, there is a need to provide dual selective $\alpha_{1a}$/ $\alpha_{1d}$ adrenoreceptor antagonists, in other words compounds that interact both with the $\alpha_{1a}$ or/and $\alpha_{1d}$ adrenoreceptor but do not interact (or at least interact substantially less) with the $\alpha_{1b}$ adrenoreceptor. The compounds of this invention can be more efficacious drugs mainly for BPH/LUTS patients, and at the same time these compounds should show less unwanted side effects than the existing pharmaceuticals.

SUMMARY OF THE INVENTION

The present invention provides a piperidine substituted cyclohexane-1,4-diamine compound of Formula (I)

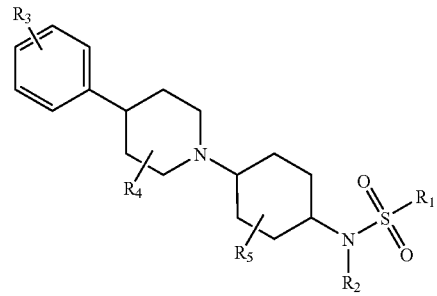

and pharmaceutically acceptable forms thereof, wherein
R$_1$ is selected from the group consisting of
(1) aryl,
(2) aryl-C$_{1-8}$alkyl,
(3) C$_{3-8}$cycloalkyl,
(4) C$_{3-8}$cycloalkyl-C$_{1-8}$alkyl,
(5) heteroaryl,
(6) heteroaryl-C$_{1-8}$alkyl,
(7) heterocyclyl, and
(8) heterocyclyl-C$_{1-8}$alkyl,
wherein each aryl, C$_{3-8}$cycloalkyl, heteroaryl and heterocyclyl is optionally substituted with one, two, three or four substituents independently selected from the group consisting of
(i) C$_{1-8}$alkyl,
(ii) C$_{1-8}$alkoxy,
(iii) C$_{1-8}$alkyl(C$_{1-8}$alkoxy),
(iv) halo-C$_{1-8}$alkyl,
(v) halo-C$_{1-8}$alkoxy,
(vi) hydroxy-C$_{1-8}$alkyl,
(vii) C$_{1-8}$alkoxy-carbonyl,
(viii) SO$_2$ substituted with a substituent selected from the group consisting of C$_{1-8}$alkyl, C$_{3-8}$cycloalkyl, aryl, heteroaryl, and heterocyclyl,
(ix) amino optionally mono- or di-substituted with C$_{1-8}$alkyl,
(x) cyano,
(xi) halogen,
(xii) hydroxy, (xiii) nitro,
(xiv) amino-$C_{1-8}$alkyl optionally mono- or di-substituted on amino with $C_{1-8}$alkyl,
(xv) aryl-$C_{1-8}$alkyl,
(xvi) aryl-$C_{1-8}$alkoxy,
(xvii) heteroaryl-$C_{1-8}$alkyl,
(xviii) heterocyclyl-$C_{1-8}$alkyl;
(xix) C(O) substituted with a substituent selected from the group consisting of hydrogen, $C_{1-8}$alkyl, $C_{3-8}$cycloalkyl, aryl, heteroaryl, and heterocyclyl,
(xx) S(O) substituted with a substituent selected from the group consisting of $C_{1-8}$alkyl, $C_{3-8}$cycloalkyl, aryl, heteroaryl, and heterocyclyl,
(xxi) C(O)N substituted on nitrogen with two substituents selected from the group consisting of hydrogen, $C_{1-8}$alkyl, $C_{3-8}$cycloalkyl, aryl, heteroaryl, and heterocyclyl,
(xxii) $SO_2$N substituted on nitrogen with two substituents selected from the group consisting of hydrogen, $C_{1-8}$alkyl, $C_{3-8}$cycloalkyl, aryl, heteroaryl, and heterocyclyl,
(xxiii) $NHSO_2$ substituted on sulfur with a substituent selected from the group consisting of $C_{1-8}$alkyl, $C_{3-8}$cycloalkyl, aryl, heteroaryl, and heterocyclyl,
(xxiv) NHC(O) substituted on carbonyl with a substituent selected from the group consisting of hydrogen, $C_{1-8}$alkyl, $C_{3-8}$cycloalkyl, aryl, heteroaryl, and heterocyclyl,
(xxv) $NHSO_2$N substituted on nitrogen with two substituents selected from the group consisting of hydrogen, $C_{1-8}$alkyl, $C_{3-8}$cycloalkyl, aryl, heteroaryl, and heterocyclyl,
(xxvi) NHC(O)N substituted on nitrogen with two substituents selected from the group consisting of hydrogen, $C_{1-8}$alkyl, $C_{3-8}$cycloalkyl, aryl, heteroaryl, and heterocyclyl,
(xxvii) $C_{3-8}$cycloalkyl,
(xxviii) aryl,
(xxix) heteroaryl, and
(xxx) heterocyclyl;
$R_2$ is selected from the group consisting of hydrogen and $C_{1-8}$alkyl;
$R_3$ is one, two, three or four optionally present substituents independently selected from the group consisting of
(1) $C_{1-8}$alkyl,
(2) $C_{1-8}$alkoxy,
(3) $C_{1-8}$alkoxy-$C_{1-8}$alkyl,
(4) halo-$C_{1-8}$alkyl,
(5) halo-$C_{1-8}$alkoxy,
(6) hydroxy-$C_{1-8}$alkyl,
(7) $C_{1-8}$alkoxy-carbonyl,
(8) $SO_2$ substituted with a substituent selected from the group consisting of $C_{1-8}$alkyl, $C_{3-8}$cycloalkyl, aryl, heteroaryl, and heterocyclyl,
(9) amino optionally mono- or di-substituted with $C_{1-8}$alkyl,
(10) cyano,
(11) halogen,
(12) hydroxy,
(13) nitro,
(14) amino-$C_{1-8}$alkyl optionally mono- or di-substituted on amino with $C_{1-8}$alkyl,
(15) aryl,
(16) aryl-$C_{1-8}$alkyl,
(17) aryl-$C_{1-8}$alkoxy,
(18) $C_{3-8}$cycloalkyl,
(19) $C_{3-8}$cycloalkyl-$C_{1-8}$alkyl,
(20) $C_{3-8}$cycloalkyl-$C_{1-8}$alkoxy,
(21) heteroaryl,
(22) heteroaryl-$C_{1-8}$alkyl,
(23) heterocyclyl,
(24) heterocyclyl-$C_{1-8}$alkyl,
(25) C(O) substituted with a substituent selected from the group consisting of hydrogen, $C_{1-8}$alkyl, $C_{3-8}$cycloalkyl, aryl, heteroaryl, and heterocyclyl,
(26) S(O) substituted with a substituent selected from the group consisting of $C_{1-8}$alkyl, $C_{3-8}$cycloalkyl, aryl, heteroaryl, and heterocyclyl,
(27) $SO_2$ substituted with a substituent selected from the group consisting of $C_{1-8}$alkyl, $C_{3-8}$cycloalkyl, aryl, heteroaryl, and heterocyclyl,
(28) C(O)N substituted on nitrogen with two substituents selected from the group consisting of hydrogen, $C_{1-8}$alkyl, $C_{3-8}$cycloalkyl, aryl, heteroaryl, and heterocyclyl,
(29) $SO_2$N substituted on nitrogen with two substituents selected from the group consisting of hydrogen, $C_{1-8}$alkyl, $C_{3-8}$cycloalkyl, aryl, heteroaryl, and heterocyclyl,
(30) $NHSO_2$ substituted on sulfur with a substituent selected from the group consisting of $C_{1-8}$alkyl, $C_{3-8}$cycloalkyl, aryl, heteroaryl, and heterocyclyl,
(31) NHC(O) substituted on carbonyl with a substituent selected from the group consisting of hydrogen, $C_{1-8}$alkyl, $C_{3-8}$cycloalkyl, aryl, heteroaryl, and heterocyclyl,
(32) $NHSO_2$N substituted on nitrogen with two substituents selected from the group consisting of hydrogen, $C_{1-8}$alkyl, $C_{3-8}$cycloalkyl, aryl, heteroaryl, and heterocyclyl,
(33) NHC(O)N substituted on nitrogen with two substituents selected from the group consisting of hydrogen, $C_{1-8}$alkyl, $C_{3-8}$cycloalkyl, aryl, heteroaryl, and heterocyclyl, and
(34) $C_{3-8}$cycloalkoxy;
wherein each aryl, $C_{3-8}$cycloalkyl, heteroaryl and heterocyclyl is optionally substituted with one or two substituents independently selected from the group consisting of
(i) $C_{1-8}$alkyl,
(ii) $C_{1-8}$alkoxy,
(iii) $C_{1-8}$alkoxy-$C_{1-8}$alkyl,
(iv) halo-$C_{1-8}$alkyl,
(v) halo-$C_{1-8}$alkoxy,
(vi) hydroxy-$C_{1-8}$alkyl,
(vii) $C_{1-8}$alkoxy-carbonyl,
(viii) $C_{1-8}$alkyl-sulfonyl,
(ix) amino optionally mono- or di-substituted with $C_{1-8}$alkyl,
(x) cyano,
(xi) halogen,
(xii) hydroxy,
(xiii) nitro, and
(xiv) amino-$C_{1-8}$alkyl optionally mono- or di-substituted on amino with $C_{1-8}$alkyl; and
$R_4$ and $R_5$ is each selected from hydrogen or are one or two optionally present substituents independently selected from the group consisting of $C_{1-8}$alkyl, $C_{1-8}$alkoxy, amino, $C_{1-8}$alkyl-amino, cyano, halogen, oxo and nitro.

Examples of the invention include pharmaceutical compositions comprising a therapeutically effective amount of any of the compounds of Formula (I) described in the present application and a pharmaceutical acceptable carrier.

An example of the invention is a pharmaceutical composition made by combining any of the compounds of Formula (I) described in the present application and a pharmaceutically acceptable carrier.

Another illustration of the invention is a process for making a pharmaceutical composition comprising combining any of the compounds described in the present application and a pharmaceutically acceptable carrier.

It is an aspect of the present invention to provide $\alpha_{1a}/\alpha_{1d}$ adrenoreceptor modulators, more specifically inhibitors thereof, more interestingly antagonists thereof. The compounds of the present invention are preferably selective dual $\alpha_{1a}/\alpha_{1d}$ adrenoceptor modulators, more specifically inhibitors thereof, more interestingly antagonists thereof.

In another aspect, the invention is directed to methods for preventing contractions of the prostate, bladder and other organs of the lower urinary tract without substantially affecting blood pressure, by administering a compound of Formula (I) described in the present application or a pharmaceutical form comprising it to a mammal (including a human) suffering from contractions of the bladder and other organs of the lower urinary tract in an amount effective for the particular use.

A further object of the present invention is a method of treatment of a patient suffering from Benign Prostatic Hyperplasia (BPH), the method comprising administering an effective amount of a compound of Formula (I) described in the present application or a pharmaceutical form comprising it to a patient suffering from BPH.

A further object of the present invention is a method for the treatment of lower-urinary-tract-symptoms (LUTS), which include, but are not limited to, filling symptoms, urgency, incontinence and nocturia, as well as voiding problems such as weak stream, hesitancy, intermittency, incomplete bladder emptying and abdominal straining, the method comprising administering an effective amount of a compound of Formula (I) described in the present application or a pharmaceutical form comprising it to a patient in need of such treatment.

A further object of the present invention is the use of these compounds as a medicine.

Yet another object of the present invention is the use of a compound of the present invention for the manufacture of a medicament for treating BPH and/or LUTS.

Still another object of the present invention is a method for treating of BPH and/or LUTS, the method comprising administering a therapeutically effective amount of a compound of the present invention in combination with an effective amount of a 5α-reductase agent, such as, for example, finasteride or durasteride.

Still another object of the present invention is method for treating of BPH and/or LUTS, the method comprising administering a therapeutically effective amount of a compound of the present invention in combination with a therapeutically effective amount of a NK-1 inhibitor.

It is still another object of the present invention to provide methods for treating of BPH and/or LUTS, the method comprising administering an therapeutically effective amount of a compound of the present invention in combination with a therapeutically effective amount of anti-antiandrogens, androgen receptor antagonists, selective androgen receptor modulators, a PDE inhibitor, urinary incontinence drugs (e.g. anti-muscarinics) or 5HT-receptor modulators.

DETAILED DESCRIPTION OF THE INVENTION

It should be understood that all compounds described and listed herein are meant to include all hydrates, solvates, polymorphs and pharmaceutically acceptable salts thereof. It should also be understood that unless otherwise indicated compounds of Formula (I) are meant to comprise the stereochemically isomeric forms thereof.

The present invention provides a piperidine substituted cyclohexane-1,4-diamine compound of Formula (I)

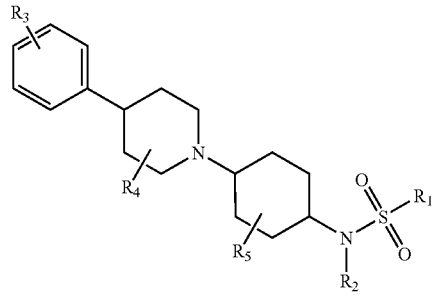

and pharmaceutically acceptable forms thereof, wherein $R_1$ is selected from the group consisting of (1) aryl, and (2) heterocyclyl, wherein each is optionally substituted with one, two, three or four substituents independently selected from the group consisting of (i) $C_{1-8}$alkyl, (ii) $C_{1-8}$alkoxy, (iii) halo-$C_{1-8}$alkoxy, and (iv) halogen.

An example of the present invention includes a compound of Formula (I) and pharmaceutically acceptable forms thereof, wherein $R_1$ is selected from the group consisting of (1) aryl optionally substituted with one, two, three or four substituents independently selected from the group consisting of (i) $C_{1-8}$alkyl, (ii) $C_{1-8}$alkoxy, (iii) halo-$C_{1-8}$alkoxy, and (iv) halogen, and (2) heterocyclyl.

An example of the present invention includes a compound of Formula (I) and pharmaceutically acceptable forms thereof, wherein $R_2$ is hydrogen.

An example of the present invention includes a compound of Formula (I) and pharmaceutically acceptable forms thereof, wherein $R_3$ is one, two, three or four optionally present substituents independently selected from the group consisting of (1) $C_{1-8}$alkyl, (2) $C_{1-8}$alkoxy, (3) halo-$C_{1-8}$alkoxy, and (4) $C_{3-8}$cycloalkyl-$C_{1-8}$alkoxy.

An example of the present invention includes a compound of Formula (I) and pharmaceutically acceptable forms thereof, wherein $R_4$ and $R_5$ are both hydrogen.

An example of the present invention includes a compound of Formula (I) selected from a compound of Formula (Ia):

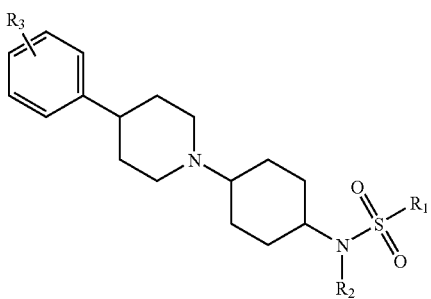

and pharmaceutically acceptable forms thereof, wherein
$R_1$ is selected from the group consisting of
(1) aryl,
(2) aryl-$C_{1-8}$alkyl,
(3) $C_{3-8}$cycloalkyl,
(4) $C_{3-8}$cycloalkyl-$C_{1-8}$alkyl,
(5) heteroaryl,
(6) heteroaryl-$C_{1-8}$alkyl,
(7) heterocyclyl, and
(8) heterocyclyl-$C_{1-8}$alkyl,
wherein each aryl, $C_{3-8}$cycloalkyl, heteroaryl and heterocyclyl is optionally substituted with one, two, three or four substituents independently selected from the group consisting of
(i) $C_{1-8}$alkyl,
(ii) $C_{1-8}$alkoxy,
(iii) $C_{1-8}$alkoxy-$C_{1-8}$alkyl,
(iv) halo-$C_{1-8}$alkyl,
(v) halo-$C_{1-8}$alkoxy,
(vi) hydroxy-$C_{1-8}$alkyl,
(vii) $C_{1-8}$alkoxy-carbonyl,
(viii) $SO_2$ substituted with a substituent selected from the group consisting of $C_{1-8}$alkyl, $C_{3-8}$cycloalkyl, aryl, heteroaryl, and heterocyclyl,
(ix) amino optionally mono- or di-substituted with $C_{1-8}$alkyl,
(x) cyano,
(xi) halogen,
(xii) hydroxy,
(xiii) nitro,
(xiv) amino-$C_{1-8}$alkyl optionally mono- or di-substituted on amino with $C_{1-8}$alkyl,
(xv) aryl-$C_{1-8}$alkyl,
(xvi) aryl-$C_{1-8}$alkoxy,
(xvii) heteroaryl-$C_{1-8}$alkyl,
(xviii) heterocyclyl-$C_{1-8}$alkyl;
(xix) C(O) substituted with a substituent selected from the group consisting of hydrogen, $C_{1-8}$alkyl, $C_{3-8}$cycloalkyl, aryl, heteroaryl, and heterocyclyl,
(xx) S(O) substituted with a substituent selected from the group consisting of $C_{1-8}$alkyl, $C_{3-8}$cycloalkyl, aryl, heteroaryl, and heterocyclyl,
(xxi) C(O)N substituted on nitrogen with two substituents selected from the group consisting of hydrogen, $C_{1-8}$alkyl, $C_{3-8}$cycloalkyl, aryl, heteroaryl, and heterocyclyl,
(xxii) $SO_2$N substituted on nitrogen with two substituents selected from the group consisting of hydrogen, $C_{1-8}$alkyl, $C_{3-8}$cycloalkyl, aryl, heteroaryl, and heterocyclyl,
(xxiii) $NHSO_2$ substituted on sulfur with a substituent selected from the group consisting of $C_{1-8}$alkyl, $C_{3-8}$cycloalkyl, aryl, heteroaryl, and heterocyclyl,
(xxiv) NHC(O) substituted on carbonyl with a substituent selected from the group consisting of hydrogen, $C_{1-8}$alkyl, $C_{3-8}$cycloalkyl, aryl, heteroaryl, and heterocyclyl,
(xxv) $NHSO_2$N substituted on nitrogen with two substituents selected from the group consisting of hydrogen, $C_{1-8}$alkyl, $C_{3-8}$cycloalkyl, aryl, heteroaryl, and heterocyclyl,
(xxvi) NHC(O)N substituted on nitrogen with two substituents selected from the group consisting of hydrogen, $C_{1-8}$alkyl, $C_{3-8}$cycloalkyl, aryl, heteroaryl, and heterocyclyl,
(xxvii) $C_{3-8}$cycloalkyl,
(xxviii) aryl,
(xxix) heteroaryl, and
(xxx) heterocyclyl;
$R_2$ is selected from the group consisting of hydrogen and $C_{1-8}$alkyl; and
$R_3$ is one, two, three or four optionally present substituents independently selected from the group consisting of
(1) $C_{1-8}$alkyl,
(2) $C_{1-8}$alkoxy,
(3) $C_{1-8}$alkoxy-$C_{1-8}$alkyl,
(4) halo-$C_{1-8}$alkyl,
(5) halo-$C_{1-8}$alkoxy,
(6) hydroxy-$C_{1-8}$alkyl,
(7) $C_{1-8}$alkoxy-carbonyl,
(8) $SO_2$ substituted with a substituent selected from the group consisting of $C_{1-8}$alkyl, $C_{3-8}$cycloalkyl, aryl, heteroaryl, and heterocyclyl,
(9) amino optionally mono- or di-substituted with $C_{1-8}$alkyl,
(10) cyano,
(11) halogen,
(12) hydroxy,
(13) nitro,
(14) amino-$C_{1-8}$alkyl optionally mono- or di-substituted on amino with $C_{1-8}$alkyl,
(15) aryl,
(16) aryl-$C_{1-8}$alkyl,
(17) aryl-$C_{1-8}$alkoxy,
(18) $C_{3-8}$cycloalkyl,
(19) $C_{3-8}$cycloalkyl-$C_{1-8}$alkyl,
(20) $C_{3-8}$cycloalkyl-$C_{1-8}$alkoxy,
(21) heteroaryl,
(25) heteroaryl-$C_{1-8}$alkyl,
(26) heterocyclyl,
(27) heterocyclyl-$C_{1-8}$alkyl,
(25) C(O) substituted with a substituent selected from the group consisting of hydrogen, $C_{1-8}$alkyl, $C_{3-8}$cycloalkyl, aryl, heteroaryl, and heterocyclyl.
(26) S(O) substituted with a substituent selected from the group consisting of $C_{1-8}$alkyl, $C_{3-8}$cycloalkyl, aryl, heteroaryl, and heterocyclyl,
(27) $SO_2$ substituted with a substituent selected from the group consisting of $C_{1-8}$alkyl, $C_{3-8}$cycloalkyl, aryl, heteroaryl, and heterocyclyl,
(28) C(O)N substituted on nitrogen with two substituents selected from the group consisting of hydrogen, $C_{1-8}$alkyl, $C_{3-8}$cycloalkyl, aryl, heteroaryl, and heterocyclyl,
(29) $SO_2$N substituted on nitrogen with two substituents selected from the group consisting of hydrogen, $C_{1-8}$alkyl, $C_{3-8}$cycloalkyl, aryl, heteroaryl, and heterocyclyl,
(30) $NHSO_2$ substituted on sulfur with a substituent selected from the group consisting of $C_{1-8}$alkyl, $C_{3-8}$cycloalkyl, aryl, heteroaryl, and heterocyclyl,
(31) NHC(O) substituted on carbonyl with a substituent selected from the group consisting of hydrogen, $C_{1-8}$alkyl, $C_{3-8}$cycloalkyl, aryl, heteroaryl, and heterocyclyl,

(32) NHSO₂N substituted on nitrogen with two substituents selected from the group consisting of hydrogen, $C_{1-8}$alkyl, $C_{3-8}$cycloalkyl, aryl, heteroaryl, and heterocyclyl,

(33) NHC(O)N substituted on nitrogen with two substituents selected from the group consisting of hydrogen, $C_{1-8}$alkyl, $C_{3-8}$cycloalkyl, aryl, heteroaryl, and heterocyclyl, and

(34) $C_{3-8}$cycloalkoxy;

wherein each aryl, $C_{3-8}$cycloalkyl, heteroaryl and heterocyclyl is optionally substituted with one or two substituents independently selected from the group consisting of (i) $C_{1-8}$alkyl,
(ii) $C_{1-8}$alkoxy,
(iii) $C_{1-8}$alkoxy-$C_{1-8}$alkyl,
(iv) halo-$C_{1-8}$alkyl,
(v) halo-$C_{1-8}$alkoxy,
(vi) hydroxy-$C_{1-8}$alkyl,
(vii) $C_{1-8}$alkoxy-carbonyl,
(viii) $C_{1-8}$alkyl-sulfonyl,
(ix) amino optionally mono- or di-substituted with $C_{1-8}$alkyl,
(x) cyano,
(xi) halogen,
(xii) hydroxy,
(xiii) nitro, and
(xiv) amino-$C_{1-8}$alkyl optionally mono- or di-substituted on amino with $C_{1-8}$alkyl.

An example of the present invention includes a compound of Formula (Ia) and pharmaceutically acceptable forms thereof, wherein $R_1$ is selected from the group consisting of (1) aryl, and
(2) heterocyclyl, wherein each is optionally substituted with one, two, three or four substituents independently selected from the group consisting of (i) $C_{1-8}$alkyl,
(ii) $C_{1-8}$alkoxy,
(iii) halo-$C_{1-8}$alkoxy, and
(iv) halogen.

An example of the present invention includes a compound of Formula (Ia) and pharmaceutically acceptable forms thereof, wherein $R_1$ is selected from the group consisting of (1) aryl optionally substituted with one, two, three or four substituents independently selected from the group consisting of
   (i) $C_{1-8}$alkyl,
   (ii) $C_{1-8}$alkoxy,
   (iii) halo-$C_{1-8}$alkoxy, and
   (iv) halogen, and
(2) heterocyclyl.

An example of the present invention includes a compound of Formula (Ia) and pharmaceutically acceptable forms thereof, wherein $R_2$ is hydrogen.

An example of the present invention includes a compound of Formula (Ia) and pharmaceutically acceptable forms thereof, wherein $R_3$ is one, two, three or four optionally present substituents independently selected from the group consisting of (1) $C_{1-8}$alkyl,
(2) $C_{1-8}$alkoxy,
(3) halo-$C_{1-8}$alkoxy, and
(4) $C_{3-8}$cycloalkyl-$C_{1-8}$alkoxy.

An example of the present invention includes a compound of Formula (I) selected from a compound of Formula (Ib):

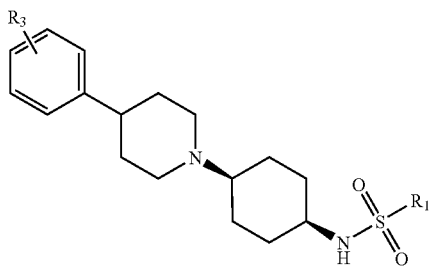

and pharmaceutically acceptable forms thereof, wherein $R_1$ and $R_3$ are dependently selected from:

| Cpd | $R_1$ | $R_3$ |
| --- | --- | --- |
| 1 | 3,4-(OCH₃)₂-phenyl | 2-OCH(CH₃)₂ |
| 3 | 3,4-F₂-phenyl | 2-OCH(CH₃)₂ |
| 5 | 3,4-(OCH₃)₂-phenyl | 2-OCH₂CF₃ |
| 7 | 3,4-(OCH₃)₂-phenyl | 2-cyclopropoxy |
| 9 | 5-Cl-2-OCH₃-phenyl | 2-cyclopropoxy |
| 11 | 5-Cl-2-F-phenyl | 2-cyclopropoxy |
| 13 | 2,3-dihydro-benzo[1,4]dioxin-6-yl | 2-OCH₂CF₃ |
| 15 | 2,4-Cl₂-phenyl | 2-cyclopropoxy |
| 17 | 5-Cl-2-OCH₃-phenyl | 2-OCH₂CF₃ |
| 19 | 5-Cl-2-F-phenyl | 2-OCH₂CF₃ |
| 21 | benzo[1,3]dioxol-5-yl | 2-cyclopropoxy |
| 23 | 3-OCHF₂-phenyl | 2-OCH₂CF₃ |
| 25 | 4-OCHF₂-phenyl | 2-OCH₂CF₃ |
| 27 | 3,4-(OCH₃)₂-phenyl | 2-O(CH₂)₃F |
| 29 | 3,4-(OCH₃)₂-phenyl | 2-OCH₂CH(F₂) |
| 31 | 3,4-(OCH₃)₂-phenyl | 4-F-2-OCH(CH₃)₂ |
| 33 | 3,4-(OCH₃)₂-phenyl | 5-F-2-OCH(CH₃)₂ |

An example of the present invention includes a compound of Formula (Ib) and pharmaceutically acceptable forms thereof, wherein $R_1$ is selected from 3,4-(OCH₃)₂-phenyl, 3,4-F₂-phenyl, 5-Cl-2-OCH₃-phenyl, 5-Cl-2-F-phenyl, 2,3-dihydrobenzo[1,4]dioxin-6-yl, 2,4-Cl₂-phenyl, benzo[1,3]dioxol-5-yl, 3-OCHF₂-phenyl and 4-OCHF₂-phenyl; and $R_3$ is selected from 2-OCH(CH₃)₂, 2-OCH₂CF₃, 2-cyclopropoxy, 2-O(CH₂)₃F, 2-OCH₂CH(F₂), 4-F-2-OCH(CH₃)₂ and 5-F-2-OCH(CH₃)₂.

An example of the present invention includes a compound of Formula (I) selected from a compound of Formula (Ic):

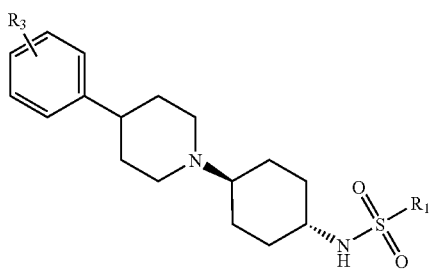

and pharmaceutically acceptable forms thereof, wherein $R_1$, and $R_3$ are dependently selected from:

| Cpd | $R_1$ | $R_3$ |
| --- | --- | --- |
| 2 | 3,4-$(OCH_3)_2$-phenyl | 2-$OCH(CH_3)_2$ |
| 4 | 3,4-$F_2$-phenyl | 2-$OCH(CH_3)_2$ |
| 6 | 3,4-$(OCH_3)_2$-phenyl | 2-$OCH_2CF_3$ |
| 8 | 3,4-$(OCH_3)_2$-phenyl | 2-cyclopropoxy |
| 10 | 5-Cl-2-$OCH_3$-phenyl | 2-cyclopropoxy |
| 12 | 5-Cl-2-F-phenyl | 2-cyclopropoxy |
| 14 | 2,3-dihydro-benzo[1,4]dioxin-6-yl | 2-$OCH_2CF_3$ |
| 16 | 2,4-$Cl_2$-phenyl | 2-cyclopropoxy |
| 18 | 5-Cl-2-$OCH_3$-phenyl | 2-$OCH_2CF_3$ |
| 20 | 5-Cl-2-F-phenyl | 2-$OCH_2CF_3$ |
| 22 | benzo[1,3]dioxol-5-yl | 2-cyclopropoxy |
| 24 | 3-$OCHF_2$-phenyl | 2-$OCH_2CF_3$ |
| 26 | 4-$OCHF_2$-phenyl | 2-$OCH_2CF_3$ |
| 28 | 3,4-$(OCH_3)_2$-phenyl | 2-$O(CH_2)_3F$ |
| 30 | 3,4-$(OCH_3)_2$-phenyl | 2-$OCH_2CH(F_2)$ |
| 32 | 3,4-$(OCH_3)_2$-phenyl | 4-F-2-$OCH(CH_3)_2$ |
| 34 | 3,4-$(OCH_3)_2$-phenyl | 5-F-2-$OCH(CH_3)_2$ |

An example of the present invention includes a compound of Formula (Ic) and pharmaceutically acceptable forms thereof, wherein $R_1$ is selected from 3,4-$(OCH_3)_2$-phenyl, 3,4-$F_2$-phenyl, 5-Cl-2-$OCH_3$-phenyl, 5-Cl-2-F-phenyl, 2,3-dihydro-benzo[1,4]dioxin-6-yl, 2,4-$Cl_2$-phenyl, benzo[1,3]dioxol-5-yl, 3-$OCHF_2$-phenyl and 4-$OCHF_2$-phenyl; and $R_3$ is selected from 2-$OCH(CH_3)_2$, 2-$OCH_2CF_3$, 2-cyclopropoxy, 2-$O(CH_2)_3F$, 2-$OCH_2CH(F_2)$, 4-F-2-$OCH(CH_3)_2$ and 5-F-2-$OCH(CH_3)_2$.

Another example of the present invention includes a compound selected from the group consisting of

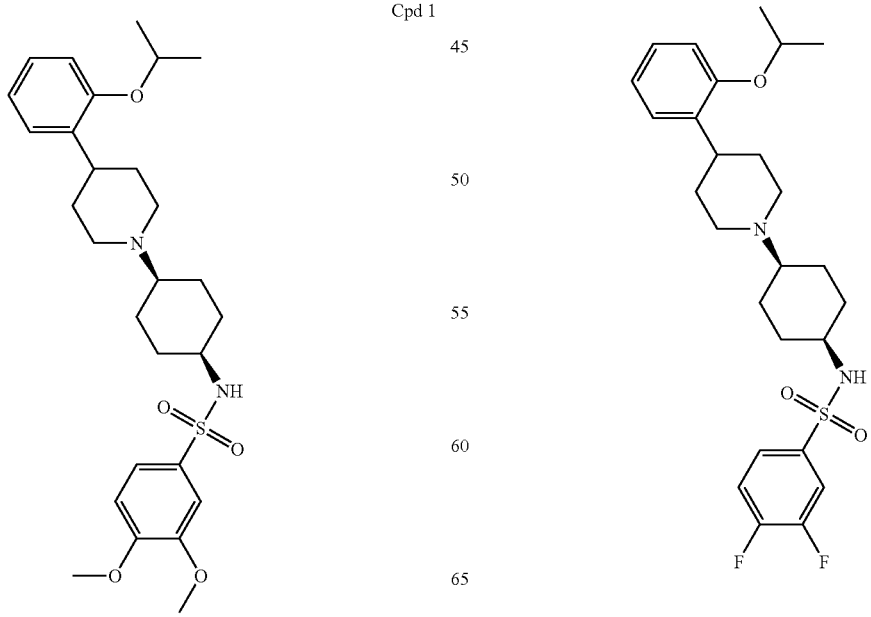

Cpd 1

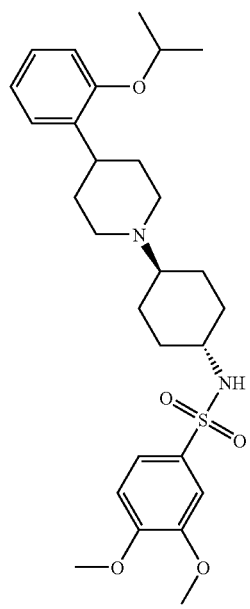

Cpd 2

Cpd 3

-continued
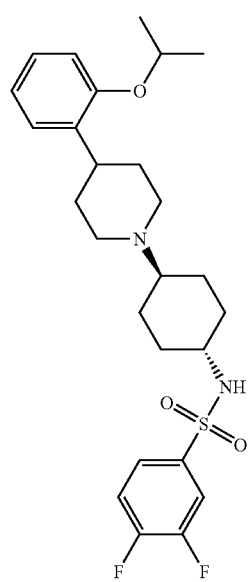
Cpd 4
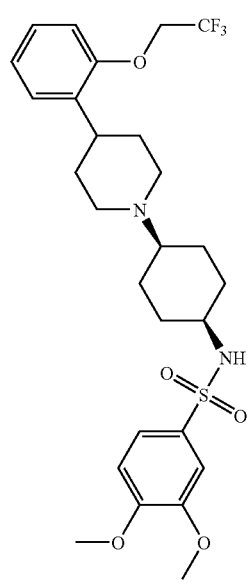
Cpd 5
-continued
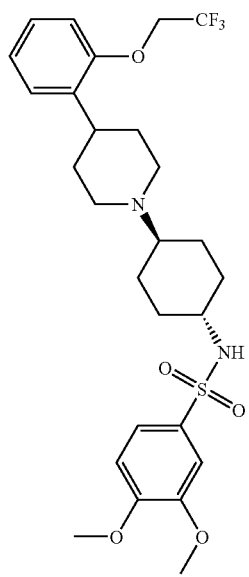
Cpd 6
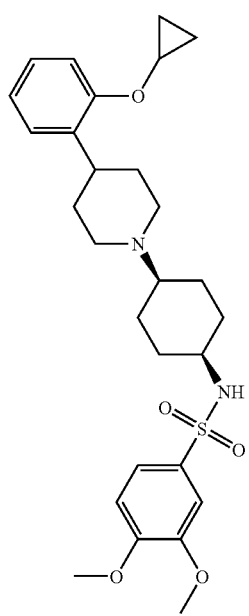
Cpd 7

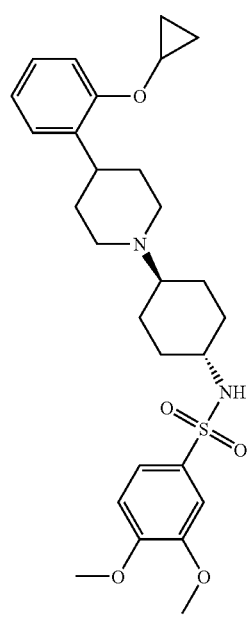
Cpd 8
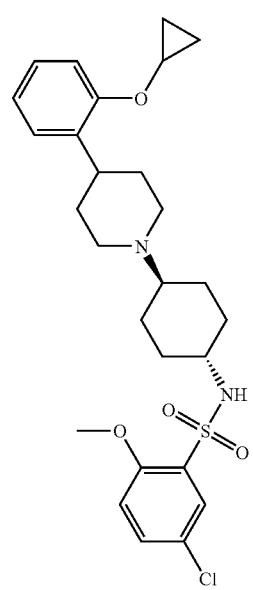
Cpd 10
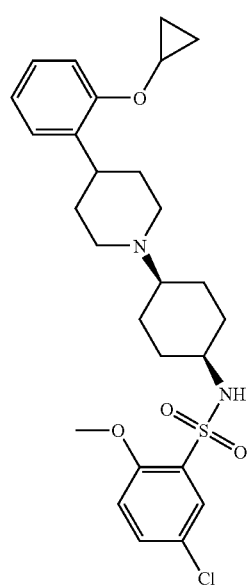
Cpd 9
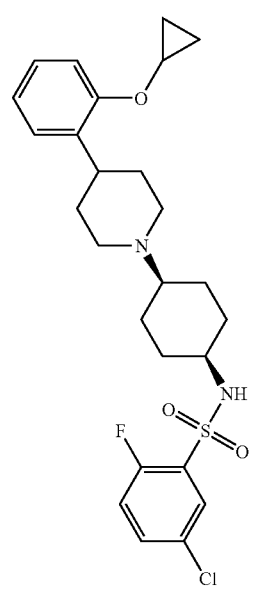
Cpd 11

-continued
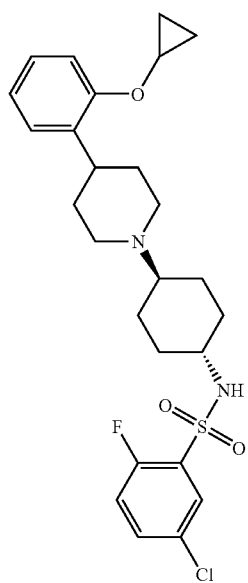
Cpd 12
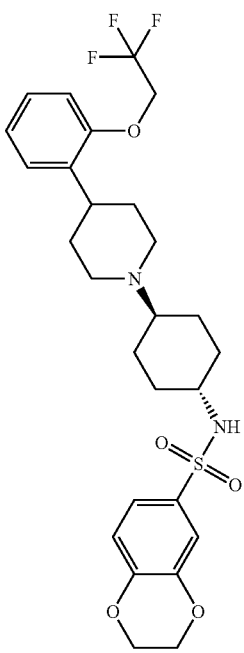
Cpd 14
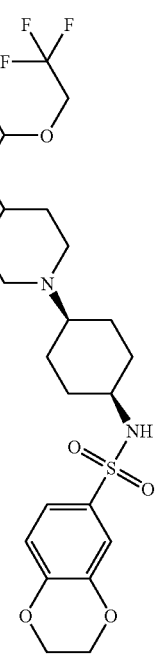
Cpd 13
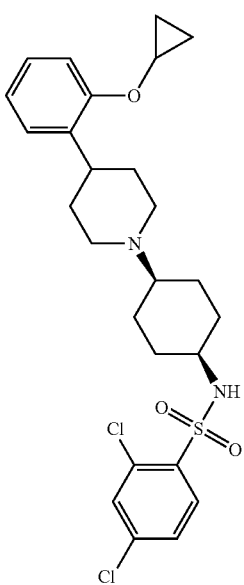
Cpd 15

-continued
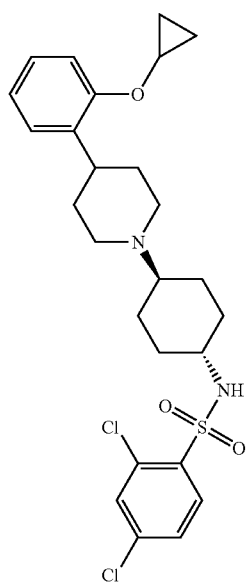
Cpd 16
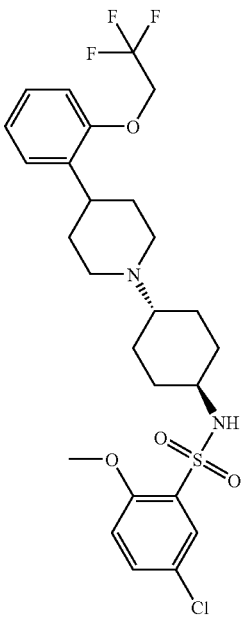
Cpd 18
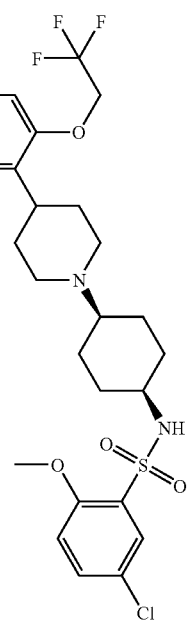
Cpd 17
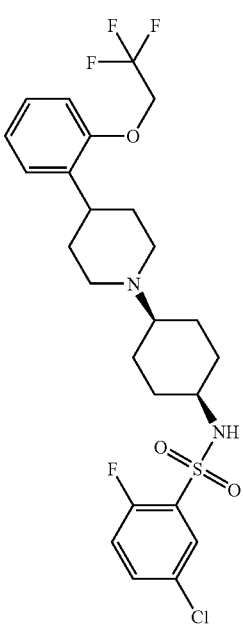
Cpd 19

-continued
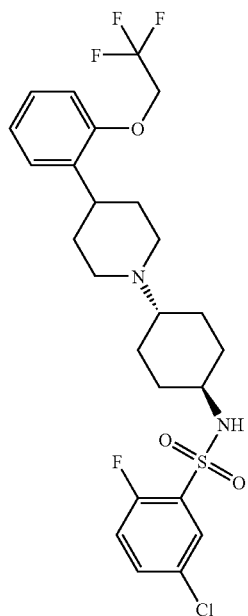
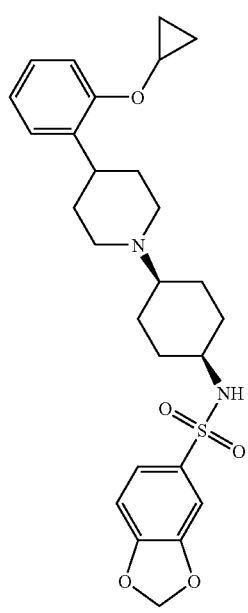
Cpd 20
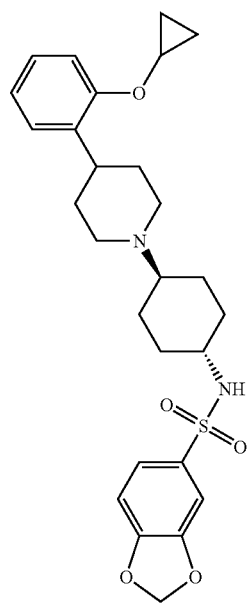
Cpd 22
Cpd 21
Cpd 23
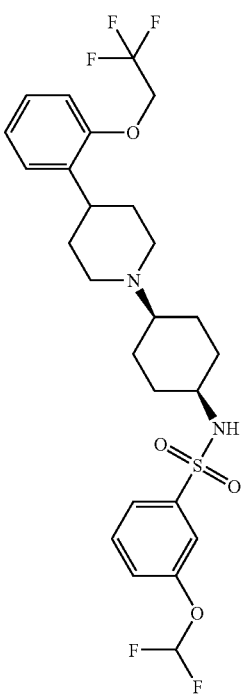

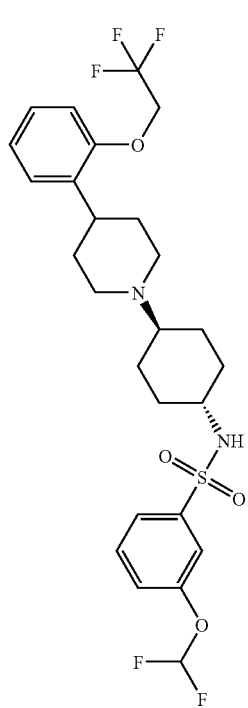
Cpd 24
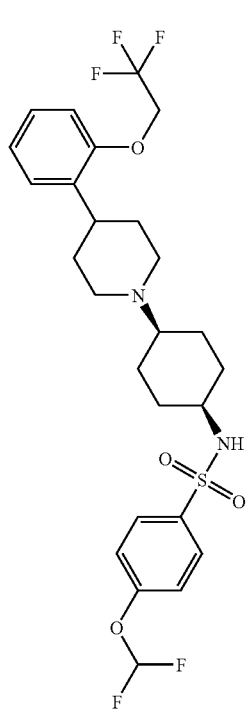
Cpd 25
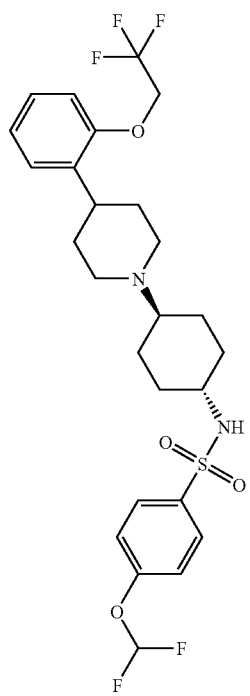
Cpd 26
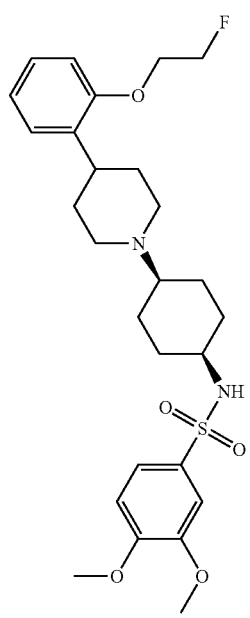
Cpd 27

-continued
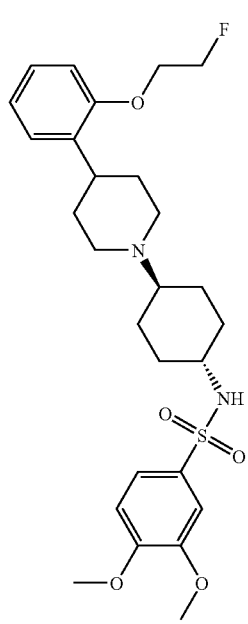
Cpd 28
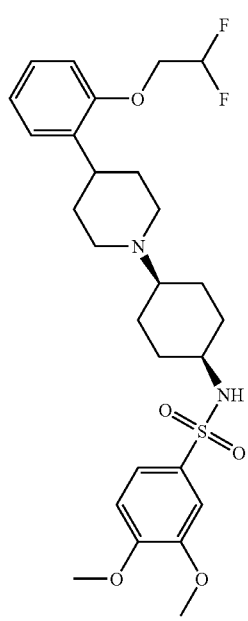
Cpd 29
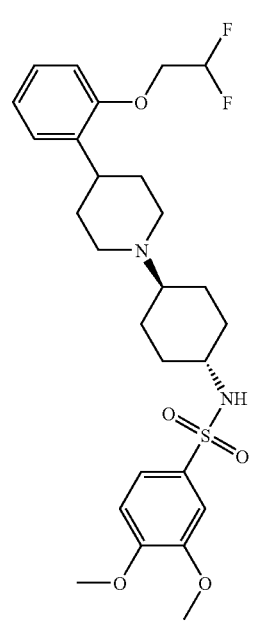
Cpd 30
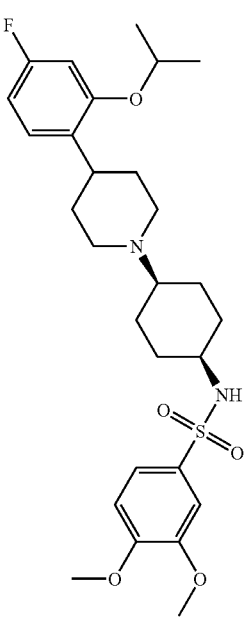
Cpd 31

-continued

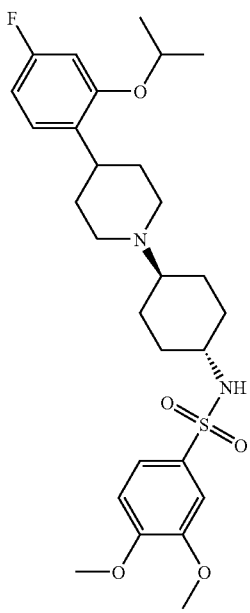

Cpd 32

Cpd 33

-continued

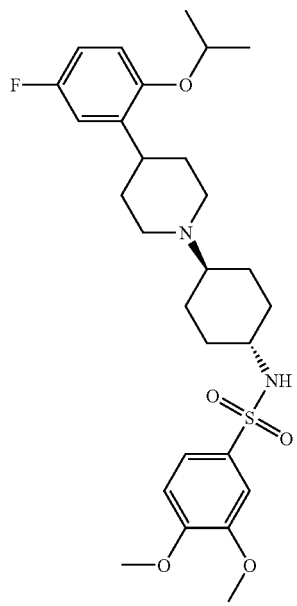

Cpd 34 and pharmaceutically acceptable forms thereof.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Certain compounds of Formula (I) may exist in various stereoisomeric or tautomeric forms and mixtures thereof. The invention encompasses all such compounds, including active compounds in the form of essentially pure enantiomers, racemic mixtures and tautomers.

The compounds of the present invention may be present in the form of pharmaceutically acceptable salts. For use in medicines, the "pharmaceutically acceptable salts" of the compounds of this invention refer to non-toxic acidic/anionic or basic/cationic salt forms. The term "pharmaceutically acceptable forms' as used herein includes "pharmaceutically acceptable salts".

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An isolated form of a chiral mixture means those forms that are substantially free of one mirror image molecule. Such substantially pure forms include those wherein one mirror image is present in a range of less than 25% in the mixture, of less than 10%, of less than 5%, of less than 2% or less than 1%.

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

"Geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations relative to a core molecule and are intended to be used as defined in the literature.

Furthermore, compounds of the present invention may have at least one crystalline, polymorph or amorphous form. The plurality of such forms are included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

Chemical Nomenclature and Definitions

Bond lines drawn into a ring system from a substituent variable indicate that the substituent may be attached to any of the substitutable ring atoms.

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$ alkyl," whether used alone or as part of a substituent group, means a straight or branched chain hydrocarbon alkyl radical or alkyldiyl linking group comprising from 1 to 8 carbon atoms, wherein the radical is derived by the removal of one hydrogen atom from a single carbon atom and the alkyldiyl linking group is derived by the removal of one hydrogen atom from each of two carbon atoms in the chain, such as, for example methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Examples include $C_{1-8}$alkyl, $C_{1-6}$alkyl and $C_{1-4}$alkyl groups. Alkyl radicals or linking groups may be attached to a core molecule via a terminal carbon atom or via a carbon atom within the chain. Similarly, substituent variables may be attached to an alkyl linking group when allowed by available valences.

The term "C$_{2-8}$alkenyl," whether used alone or as part of a substituent group, means a straight or branched chain hydrocarbon alkyl or alkyldiyl radical having at least one carbon-carbon double bond, whereby the double bond is derived by the removal of one hydrogen atom from each of two adjacent carbon atoms of the alkyl radical. Atoms may be oriented about the double bond in either the cis (E) or trans (S) conformation. Typical alkenyl groups comprising from 2 to 8 carbon atoms, such as, for example, ethenyl, propenyl, allyl (2-propenyl), butenyl, pentenyl, hexenyl and the like. Examples include C$_{2-4}$alkenyl groups.

The term "C$_{2-8}$alkynyl" whether used alone or as part of a substituent group, means a straight or branched chain hydrocarbon alkyl or alkyldiyl radical having at least one carbon-carbon triple bond, whereby the triple bond is derived by the removal of two hydrogen atoms from each of two adjacent carbon atoms of the alkyl radical. Typical alkynyl groups comprising from 2 to 8 carbon atoms, such as, for example, ethynyl, propynyl, butynyl, pentynyl, hexynyl and the like. Examples include C$_{2-4}$alkynyl groups.

The term "C$_{1-8}$alkoxy," whether used alone or as part of a substituent group, refers to an alkyl or alkyldiyl radical attached through an oxygen-linking atom, as in the formula: —O—C$_{1-8}$alkyl. Typical alkoxy groups comprising from 1 to 8 carbon atoms, such as, for example, methoxy, ethoxy, propoxy, butoxy, pentoxy, hexoxy, heptoxy, octoxy and the like. An alkoxy radical may be attached to a core molecule and further substituted where indicated. Examples include C$_{1-8}$alkoxy or C$_{1-4}$alkoxy groups.

The term "C$_{3-12}$cycloalkyl," whether used alone or as part of a substituent group, refers to a saturated or partially unsaturated, monocyclic or polycyclic hydrocarbon ring system radical derived by the removal of one hydrogen atom from a single ring carbon atom.

The term "C$_{3-12}$cycloalkyl" also includes a C$_{3-8}$cycloalkyl, C$_{3-10}$cycloalkyl, C$_{5-6}$cycloalkyl, C$_{5-8}$cycloalkyl, C$_{5-12}$cycloalkyl, C$_{9-13}$cycloalkyl or benzofused-C$_{3-12}$cycloalkyl ring system radical such as, for example, cyclopropyl, cyclobutyl, cyclopentyl, cyclohexyl, cycloheptyl, cyclooctyl, 1H-indenyl, indanyl, 9H-fluorenyl, tetrahydro-naphthalenyl, acenaphthenyl, adamantanyl and the like. Examples include C$_{3-8}$cycloalkyl, C$_{5-8}$cycloalkyl, C$_{3-10}$cycloalkyl and the like. C$_{3-12}$cycloalkyl radicals may be attached to a core molecule and further substituted on any atom when allowed by available valences.

The term "heterocyclyl," whether used alone or as part of a substituent group, refers to a saturated or partially unsaturated monocyclic or polycyclic ring radical derived by the removal of one hydrogen atom from a single carbon or nitrogen ring atom. Typical heterocyclyl radicals include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydrofuranyl, tetrahydrothienyl, tetrahydropyranyl, tetrahydro-pyridazinyl, 1,3-benzodioxolyl (also referred to as benzo[1,3]dioxolyl), 2,3-dihydro-1,4-benzodioxinyl (also referred to as 2,3-dihydro-benzo[1,4]dioxinyl) and the like. Heterocyclyl radicals may be attached to a core molecule and further substituted on any atom when allowed by available valences.

The term "hetero" used as a prefix for a ring system refers to the replacement of at least one ring carbon atom with one or more heteroatoms independently selected from N, S, or O. Examples include rings wherein 1, 2, 3 or 4 ring members are a nitrogen atom; or, 0, 1, 2 or 3 ring members are nitrogen atoms and 1 member is an oxygen or sulfur atom. When allowed by available valences, up to two adjacent ring members may be heteroatoms; wherein, for example, one heteroatom is nitrogen and the other is one heteroatom selected from N, S or O.

The term "aryl," whether used alone or as part of a substituent group, refers to an aromatic monocyclic or polycyclic hydrocarbon ring radical derived by the removal of one hydrogen atom from a single carbon atom of the ring system. Typical aryl radicals include phenyl, naphthalenyl, azulenyl, anthracenyl and the like. Aryl radicals may be attached to a core molecule and further substituted on any atom when allowed by available valences.

The term "aromatic" refers to a cycloalkyl hydrocarbon ring system having an unsaturated, conjugated π electron system.

The term "heteroaryl," whether used alone or as part of a substituent group, refers to a heteroaromatic monocyclic or polycyclic hydrocarbon ring radical derived by the removal of one hydrogen atom from a single ring carbon atom of the ring system. Typical heteroaryl radicals include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, azaindolyl, isoindolyl, benzo[b]furyl, benzo[b]thienyl, indazolyl, azaindazolyl, benzimidazolyl, benzthiazolyl, benzoxazolyl, benzisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. Heteroaryl radicals may be attached to a core molecule and further substituted on any atom when allowed by available valences.

The term "C$_{1-8}$alkoxy-C$_{1-8}$alkyl" means a radical of the formula: —C$_{1-8}$alkyl-O—C$_{1-8}$alkyl.

The term "C$_{1-8}$alkoxy-carbonyl" means a radical of the formula: —C(O)—O—C$_{1-8}$alkyl.

The term "C$_{1-8}$alkyl-amino" means a radical of the formula: —NH—C$_{1-8}$alkyl or —N(C$_{1-8}$alkyl)$_2$.

The term "C$_{1-8}$alkyl-sulfonyl" means a radical of the formula: —SO$_2$—C$_{1-8}$alkyl.

The term "amino" means a radical of the formula: —NH$_2$.

The term "amino-C$_{1-8}$alkyl" means a radical of the formula: —C$_{1-8}$alkyl-NH$_2$.

The term "aryl-C$_{1-8}$alkoxy" means a radical of the formula: —O—C$_{1-8}$alkyl-aryl.

The term "aryl-C$_{1-8}$alkyl" means a radical of the formula: —C$_{1-8}$alkyl-aryl.

The term "C$_{3-8}$cycloalkyl-C$_{1-8}$alkoxy" means a radical of the formula: —O—C$_{1-8}$alkyl-C$_{3-8}$cycloalkyl.

The term "C$_{3-8}$cycloalkyl-C$_{1-8}$alkyl" means a radical of the formula: —C$_{1-8}$alkyl-C$_{3-8}$cycloalkyl.

The term "heterocyclyl-C$_{1-8}$alkyl" means a radical of the formula: —C$_{1-8}$alkyl-heterocyclyl.

The term "heteroaryl-C$_{1-8}$alkyl" means a radical of the formula: —C$_{1-8}$alkyl-heteroaryl.

The term "halogen" or "halo" means the group fluoro, chloro, bromo or iodo.

The term "halo-C$_{1-8}$alkoxy" means a radical of the formula: —O—C$_{1-8}$alkyl-(halo)$_n$, wherein one or more halogen atoms may be substituted on C$_{1-8}$alkyl when allowed by available valences (wherein n represents that amount of available valences based on the number of carbon atoms in the chain), and includes monofluoromethyl, difluoromethyl, trifluoromethyl, trifluoroethyl and the like.

The term "halo-C$_{1-8}$alkyl" means a radical of the formula: —C$_{1-8}$alkyl-(halo)$_n$, wherein one or more halogen atoms may be substituted on $C_{1-8}$alkyl when allowed by available valences (wherein n represents that amount of available valences based on the number of carbon atoms in the chain), and includes monofluoromethyl, difluoromethyl, trifluoromethyl, trifluoroethyl and the like.

The term "hydroxy-$C_{1-8}$alkyl" means a radical of the formula: —$C_{1-8}$alkyl-hydroxy, wherein $C_{1-8}$alkyl is substituted on one or more available carbon chain atoms with one or more hydroxy radicals when allowed by available valences.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

The term "independently selected" refers to one or more substituents selected from a group of substituents variable group, wherein the selected substituents may be the same or different.

The term "dependently selected" refers to one or more substituents specified in an indicated combination of structure variables.

Therapeutic Use

The ability of compounds of the present invention to specifically bind to the $\alpha_{1a}$ as well as to the $\alpha_{1d}$ receptor makes them useful for the treatment of BPH. The specificity of binding of compounds showing affinity for the $\alpha_{1a}$ and the $\alpha_{1d}$ receptor is compared against the binding affinities to other types of alpha receptors.

An aspect of the present invention includes a compound of Formula (I) having an $IC_{50}$ (50% inhibition concentration) against the activity of either or both the $\alpha_{1a}$ and/or $\alpha_{1d}$ adrenoreceptor in a range of about 25 µM or less, of about 10 µM or less, of about 1 µM or less, of about 0.5 µM or less, of about 0.25 µM or less or of about 0.1 µM or less.

Another aspect of the present invention includes dual selective $\alpha_{1a}/\alpha_{1d}$ adrenoreceptor antagonists for treating, ameliorating or preventing a plurality of $\alpha_{1a}$ and/or $\alpha_{1d}$ adrenoreceptor mediated disorders or diseases.

The usefulness of a compound of the present invention or composition thereof as a dual selective $\alpha_{1a}/\alpha_{1d}$ adrenoreceptor antagonist can be determined according to the methods disclosed herein. The scope of such use includes the treatment of benign prostatic hypertrophy and/or lower urinary tract symptoms.

An aspect of the use for a compound of Formula (I) includes use of an instant compound as a marker, wherein the compound is labeled with a ligand such as a radioligand (selected from deuterium, tritium and the like).

The present invention is further directed to a method for treating, ameliorating or preventing an $\alpha_{1a}$ and/or $\alpha_{1d}$ adrenoreceptor mediated disorder or disease in a subject in need of such treatment, amelioration or prevention comprising administering to the subject a therapeutically or prophylactically effective amount of a compound of Formula (I) or a form or composition thereof.

An aspect of the method of the present invention further includes treating Benign Prostatic Hyperplasia in a subject in need of such treatment comprising administering to the subject in need of such treatment a therapeutically effective amount of a compound of Formula (I) or a form or composition thereof.

An aspect of the method of the present invention further includes treating Lower Urinary Tract Symptoms in a subject in need of such treatment comprising administering to the subject in need of such treatment a therapeutically effective amount of a compound of Formula (I) or a form or composition thereof.

Another aspect of the method of the present invention further includes administering to the subject an effective amount of a compound of Formula (I) or composition thereof in the form of a medicament. Consequently, the invention encompasses the use of the compound of Formula (I) as a medicament.

Accordingly, the present invention includes the use of a compound of Formula (I) for the manufacture of a medicament for treating any of the diseases, disorders or conditions mentioned in any of the foregoing methods.

The term "$\alpha_{1a}$ and/or $\alpha_{1d}$ adrenoreceptor mediated disorder or disease" means disorders or diseases such as, but not limited to, contractions of the prostate, bladder and other organs of the lower urinary tract with or without an effect on blood pressure. The scope of such use includes the treatment of BPH and/or LUTS.

The term "LUTS" means disorders or diseases such as, but not limited to, filling symptoms, urgency, incontinence and nocturia, as well as voiding problems such as weak stream, hesitancy, intermittency, incomplete bladder emptying and abdominal straining.

The present invention thereby includes a method for treating, ameliorating or preventing an $\alpha_{1a}$ and/or $\alpha_{1d}$ adrenoreceptor mediated disorder or disease in a patient in need thereof comprising administering to the patient an effective amount of a compound of Formula (I) or pharmaceutical composition thereof.

The present invention thereby includes a method for treating, ameliorating or preventing BPH and/or LUTS in a patient in need of such treatment comprising administering to the patient an effective amount of a compound of Formula (I) or pharmaceutical composition thereof.

The term "patient" or "subject" means an animal, preferably a mammal, most preferably a human, which has been a patient or the object of treatment, prevention, observation or experiment.

The term "administering" is to be interpreted liberally in accordance with the methods of the present invention. Such methods include therapeutically or prophylactically administering an effective amount of a composition or medicament of the present invention at different times during the course of a therapy or concurrently in a combination form. Prophylactic administration can occur prior to the manifestation of symptoms characteristic of an $\alpha_{1a}$ and/or $\alpha_{1d}$ adrenoreceptor mediated disorder or disease such that the disorder or disease is treated, ameliorated, prevented or otherwise delayed in its progression. The methods of the present invention are further to be understood as embracing all therapeutic or prophylactic treatment regimens used by those skilled in the art.

The term "effective amount" refers to that amount of active compound or pharmaceutical agent that elicits the biological or medicinal response in a tissue system, animal or human, that is being sought by a researcher, veterinarian, medical doctor, or other clinician, which includes treating, ameliorating or preventing the symptoms of a syndrome, disorder or disease being treated.

An effective amount of a compound of Formula (I) for use in a method of the present invention is in a range of from about 0.001 mg/kg/day to about 300 mg/kg/day.

The term "medicament" refers to a product for use in treating, preventing or ameliorating a kinase mediated disease, disorder or condition.

In an example of the method for treating, ameliorating or preventing an $\alpha_{1a}$-AR and $\alpha_{1d}$-AR mediated disorder or disease described herein, the method includes treating a patient suffering from BPH and/or LUTS comprising administering to the patient an effective amount of a combination product comprising a compound of Formula (I) or pharmaceutical composition thereof in combination with a BPH and/or LUTS therapeutic agent.

The BPH and/or LUTS therapeutic agent includes a human testosterone 5α-reductase inhibitor agent or 5-α reductase isoenzyme 2 inhibitor agent (such as finasteride or durasteride and the like or mixtures thereof), a NK-1 inhibitor, an anti-androgen receptor agonist, an androgen receptor antagonist, a selective androgen receptor modulators, a PDE inhibitor, a urinary incontinence drugs (e.g. anti-muscarinics) or a 5HT-receptor modulator.

With regard to the method for administering a combination product, the term "effective amount" means that amount of the compound of Formula (I) or pharmaceutical composition thereof in combination with that amount of the therapeutic agent that has been adjusted to treat, ameliorate or prevent the symptoms of a syndrome, disorder or disease being treated.

As those skilled in the art will appreciate, the dosages of the compound of Formula (I) or pharmaceutical composition thereof and the therapeutic agent may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Wherein the present invention is directed to the administration of a combination of a compound of Formula (I) and another agent for the treatment of BPH, the terms "therapeutically effective amount" or "prophylactically effective amount" shall mean that amount of the combination of agents taken together so that the combined effect elicits the desired biological or medicinal response.

Representative compounds of the present invention exhibit high selectivity for the $\alpha_{1a}$ and $\alpha_{1d}$ adrenergic receptor. Moreover, representative compounds of the present invention show low to very low affinity for the $\alpha_{1d}$ receptor. As a consequence thereof, the compounds of the present invention are believed to lower the intraurethral pressure without the unwanted side effects.

These compounds can be administered in dosages effective to antagonize the $\alpha_{1a}$ and $\alpha_{1d}$ receptor where such treatment is needed, as in BHP.

Pharmaceutical Compositions

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human $\alpha_{1a}$ adrenergic receptors can be administered in a wide variety of therapeutic dosage forms in conventional vehicles for systemic administration.

The present invention also provides pharmaceutical compositions comprising one or more compounds of this invention in association with a pharmaceutically acceptable carrier. Preferably these compositions are in unit dosage forms such as tablets, pills, capsules, powders, graules, sterile parenteral solutions or suspensions, metered aerosol or liquid sprays, drops, ampoules, autoinjector devices or suppositories; for oral, parenteral, intranasal, sublingual or rectal administration, or for administration by inhalation or insufflation.

In solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogenous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. An enteric layer can separate the two components. That enteric layer serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

As used herein, the term "composition" is intended to encompass a product comprising the specified ingredients in the specified amounts, as well as any product which results, directly or indirectly, from combination of the specified ingredients in the specified amounts.

An effective but non-toxic amount of the compound desired can be employed as a $\alpha_{1a}/\alpha_{1d}$ antagonistic agent. Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium and elimination of a drug.

Compounds of Formula (I) may be administered in any of the foregoing compositions and according to dosage regimens established in the art whenever inhibition of the human $\alpha_{1a}$-AR or $\alpha_{1d}$-AR is required. Such inhibition includes inhibition of the human $\alpha_{1a}$-AR or $\alpha_{1a}$-AR, selective inhibition of the human $\alpha_{1a}$-AR or $\alpha_{1a}$-AR, dual inhibition of the human $\alpha_{1a}$-AR and $\alpha_{1a}$-AR or selective, dual inhibition of the human $\alpha_{1a}$-AR and $\alpha_{1a}$-AR. The compounds of Formula (I) may be used alone at appropriate dosages defined by routine testing in order to obtain optimal antagonism of the human $\alpha_{1a}$-AR or $\alpha_{1d}$-AR while minimizing any potential toxicity.

The daily dosage of the products may be varied over a wide range from about 0.001 to about 3,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and milligrams of the active ingredient for the symptomatic adjustment of the dosage to the patient to be treated. A medicament typically contains from about 0.01 mg to about 500 mg of the active ingredient, preferably, from about 0.001 mg to about 3000 mg of active ingredient.

An example of an effective amount of a compound of Formula (I) is a dosage level range of from about 0.001 mg/kg to about 20 mg/kg of body weight per day. Preferably, the range is from about 0.001 to 10 mg/kg of body weight per day. More preferably, the range is from about 0.001 mg/kg to 7 mg/kg of body weight per day. The compounds may be administered on a regimen of 1 to 4 times per day.

Compounds of the present invention may be used alone at appropriate dosages defined by routine testing in order to obtain optimal antagonism of the human $\alpha_{1a}/\alpha_{1d}$ adrenergic receptor while minimizing any potential toxicity. In addition, co-administration or sequential administration of other agents which alleviate the effects of BPH is desirable.

When compounds of Formula (I) are administered in a combination product, the compound of Formula (I) or pharmaceutical composition thereof and the therapeutic agent may be co-administered or sequentially administered whereby the effects of BPH and/or LUTS is treated, ameliorated or prevented.

Thus, in one embodiment, the method of the present invention includes administration of compounds of this invention and a human testosterone 5-α reductase inhibitor, including inhibitors of 5-α reductase isoenzyme 2.

The dosages of the $\alpha_{1a}$ adrenergic receptor and testosterone 5-α reductase inhibitors are adjusted when combined to achieve desired effects. As those skilled in the art will appreciate, dosages of the 5-α reductase inhibitor and the $\alpha_{1a}$ adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

The effective amount of the therapeutic agent selected from a human testosterone 5α-reductase inhibitor agent or 5-α reductase isoenzyme 2 inhibitor agent (such as finasteride or durasteride and the like or mixtures thereof), a NK-1 inhibitor, an anti-androgen receptor agonist, an androgen receptor antagonist, a selective androgen receptor modulators, a PDE inhibitor, a urinary incontinence drugs (e.g. anti-muscarinics) or a 5HT-receptor modulator is a dosage level range of from about 0.0002 mg/kg to about 20 mg/kg of body weight per day. Preferably, the range is from about 0.001 to 10 mg/kg of body weight per day. More preferably, the range is from about 0.001 mg/kg to 7 mg/kg of body weight per day.

For the treatment of benign prostatic hyperplasia, compounds of this invention exhibiting $\alpha_{1a}$ adrenergic receptor antagonism can be combined with a therapeutically effective amount of a 5α-reductase isoenzyme 2 inhibitor, such as finasteride.

Thus, in one embodiment of the present invention, a method of treating BPH is provided which comprises administering to a subject in need of treatment any of the compounds of the present invention in combination with finasteride effective to treat BPH.

The dosage of finasteride administered to the subject is about 0.01 mg per subject per day to about 50 mg per subject per day in combination with an $\alpha_{1a}$ antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

In other embodiments of the present inventions, a method of treating BPH is provided which comprises administering to a subject in need of treatment any of the compounds of the present invention in combination with a therapeutically effective amount of an anti-antiandrogenic agent, androgen receptor antagonists, selective androgen receptor modulators, urinary incontinence drugs (e.g. anti-muscarinics) or 5HT-receptor modulators.

A representative compound of Formula (I) or a form thereof for use in the therapeutic methods and pharmaceutical compositions, medicines or medicaments described herein includes a compound selected from:

N-cis-{4-[4-(2-isopropoxy-phenyl)-piperidin-1-yl]-cyclohexyl}-3,4-dimethoxy-benzenesulfonamide, 3,4-difluoro-N-cis-{4-[4-(2-isopropoxy-phenyl)-piperidin-1-yl]-cyclohexyl}-benzenesulfonamide, 3,4-difluoro-N-trans-{4-[4-(2-isopropoxy-phenyl)-piperidin-1-yl]-cyclohexyl}-benzenesulfonamide, 3,4-dimethoxy-N-cis-(4-{4-[2-(2,2,2-trifluoro-ethoxy)-phenyl]-piperidin-1-yl}cyclohexyl)-benzenesulfonamide, 3,4-dimethoxy-N-trans-(4-{4-[2-(2,2,2-trifluoro-ethoxy)-phenyl]-piperidin-1-yl}-cyclohexyl)-benzenesulfonamide, N-cis-{4-[4-(2-cyclopropoxy-phenyl)-piperidin-1-yl]-cyclohexyl}-3,4-dimethoxy-benzenesulfonamide, 5-chloro-N-cis-{4-[4-(2-cyclopropoxy-phenyl)-piperidin-1-yl]-cyclohexyl}-2-methoxy-benzenesulfonamide, 5-chloro-N-cis-{4-[4-(2-cyclopropoxy-phenyl)-piperidin-1-yl]-cyclohexyl}-2-fluoro-benzenesulfonamide, 2,3-dihydro-benzo[1,4]dioxine-6-sulfonic acid cis-(4-{4-[2-(2,2,2-trifluoro-ethoxy)-phenyl]-piperidin-1-yl}-cyclohexyl)-amide, 5-chloro-2-methoxy-N-cis-(4-{4-[2-(2,2,2-trifluoro-ethoxy)-phenyl]-piperidin-1-yl}-cyclohexyl)-benzenesulfonamide, 5-chloro-2-methoxy-N-trans-(4-{4-[2-(2,2,2-trifluoro-ethoxy)-phenyl]-piperidin-1-yl}-cyclohexyl)-benzenesulfonamide, 5-chloro-2-fluoro-N-cis-(4-{4-[2-(2,2,2-trifluoro-ethoxy)-phenyl]-piperidin-1-yl}-cyclohexyl)-benzenesulfonamide,
5-chloro-2-fluoro-N-trans-(4-{4-[2-(2,2,2-trifluoro-ethoxy)-phenyl]-piperidin-1-yl}-cyclohexyl)-benzenesulfonamide,
3-difluoromethoxy-N-cis-(4-{4-[2-(2,2,2-trifluoro-ethoxy)-phenyl]-piperidin-1-yl}-cyclohexyl)-benzenesulfonamide,
N-cis-(4-{4-[2-(2-fluoro-ethoxy)-phenyl]-piperidin-1-yl}-cyclohexyl)-3,4-dimethoxy-benzenesulfonamide,
N-trans-(4-{4-[2-(2-fluoro-ethoxy)-phenyl]-piperidin-1-yl}-cyclohexyl)-3,4-dimethoxy-benzenesulfonamide,
N-cis-(4-{4-[2-(2,2-difluoro-ethoxy)-phenyl]-piperidin-1-yl}-cyclohexyl)-3,4-dimethoxy-benzenesulfonamide,
N-cis-{4-[4-(4-fluoro-2-isopropoxy-phenyl)-piperidin-1-yl]-cyclohexyl}-3,4-dimethoxy-benzenesulfonamide,
N-cis-{4-[4-(5-fluoro-2-isopropoxy-phenyl)-piperidin-1-yl]-cyclohexyl}-3,4-dimethoxy-benzenesulfonamide, and
N-trans-{4-[4-(5-fluoro-2-isopropoxy-phenyl)-piperidin-1-yl]-cyclohexyl}-3,4-dimethoxy-benzenesulfonamide.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, 3rd Edition, John Wiley & Sons, 1999. The protecting groups may be removed at a convenient subsequent stage using methods known in the art.

Synthetic Routes

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The terms used in describing the invention are commonly used and known to those skilled in the art. Some reagents are referred to as a chemical formula. Other reagents are referred to as abbreviations known to persons skilled in the art. When used herein, the following abbreviations have the indicated meanings:

Cpd compound
DCM dichloromethane
min/hr(s)/d(s) minute/hour(s)/day(s)
M.P. melting point in ° C.
MS Mass Spectrum in m/z (M+H$^+$)
RT/rt/r.t. room temperature
TEA triethylamine
THF tetrahydrofuran Specific compounds that are representative of the invention may be prepared as per the following examples offered by way of illustration and not by way of limitation. No attempt has been made to optimize the yields obtained in any of the reactions. One skilled in the art would know how to increase such yields through routine variations in reaction times, temperatures, solvents and/or reagents. Additional compounds may be made according to the synthetic methods of the present invention by one skilled in the art, differing only in possible starting materials, reagents and conditions used in the instant methods.

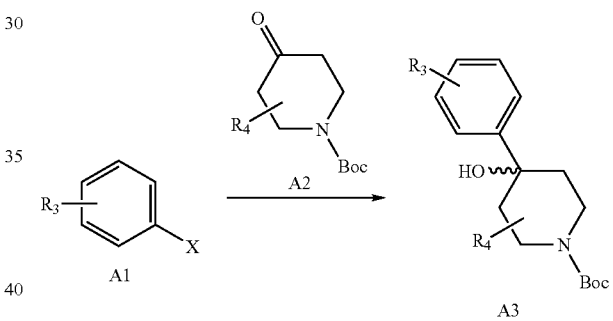

A $R_3$ substituted phenyl Compound A1 (wherein X represents a halogen atom or other suitable leaving group) is dissolved in a solvent (such as dry THF or DCM and the like) and cooled to −78° C. The solution is treated with a reagent (such as n-BuLi) at −78° C. over a short time period (about 15-30 mins.). A solution of a $R_4$ substituted 4-oxo-piperidine-1-carboxylic acid tert-butyl ester Compound A2 (in a solvent such as THF and the like) is added and the mixture is stirred at −78° C. for 5 hrs. The reaction is quenched with NH$_4$Cl (saturated). The layers are separated (using a solvent such as DCM) and the organic extracts are dried (such as over K$_2$CO$_3$). The filtered dry solution is evaporated and a crude product is obtained. The product is purified via flash chromatography (on a silica gel column, using AcOEt or a AcOEt/hexane mixture as eluent) to provide the substituted 4-phenyl-4-hydroxy-piperidine-1-carboxylic acid tert-butyl ester Compound A3.

One or more of the $R_3$ substituents for the Compound A1 starting material may be amenable for further substitution using various reagent(s) and reaction conditions, thus enabling the preparation of other compounds that are representative of the invention both as shown herein and further by one skilled in the art.

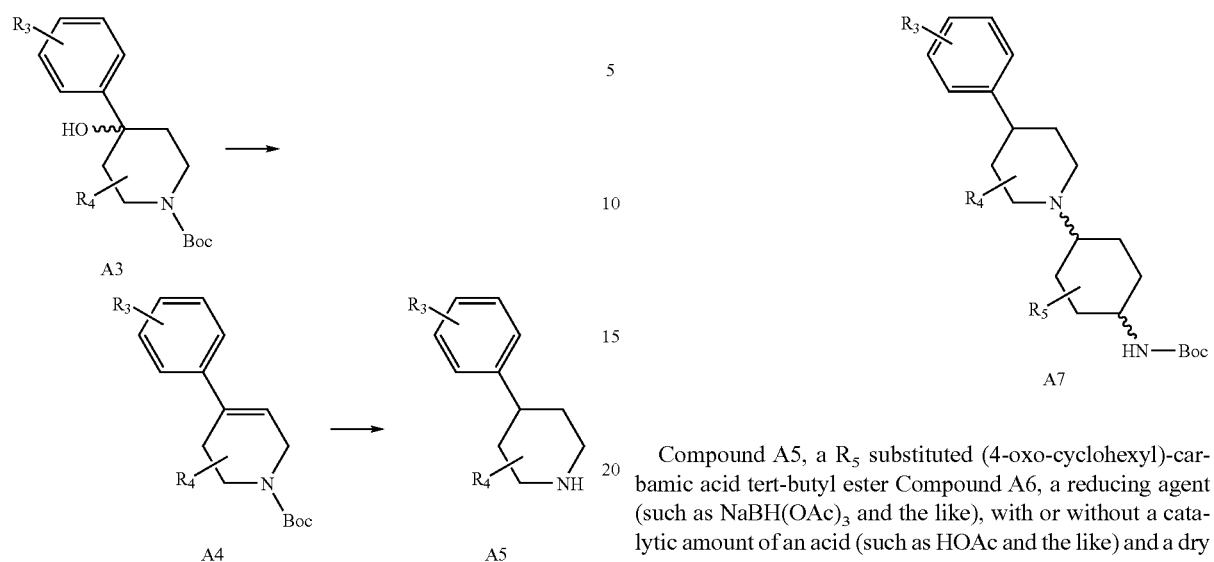

Compound A3 is dissolved in a solvent (such as dry DCM and the like) and cooled to −78° C. The solution is treated with a reagent (such as methanesulfonyl chloride) over a period of 30 mins followed by the addition of a base (such as $Et_3N$). The reaction mixture is warmed to r.t. gradually and quenched. The layers are separated and the organic extracts are dried. The filtered dry solution is evaporated and a crude product is obtained and purified via flash chromatography to provide the substituted 4-phenyl-3,6-dihydro-2H-pyridine-1-carboxylic acid tert-butyl ester Compound A4.

Compound A4 is dissolved in a solvent (such as EtOH and the like), then 10% Pt/carbon and HOAc are added. The mixture is shaken under a hydrogen atmosphere (50 psi) at r.t. for 18 hrs, then filtered through celite. Evaporation to dryness gives a piperidine intermediate, which is dissolved in a solvent (such as DCM and the like). The solution is treated with a solvent (such as TFA and the like) at r.t. over a period of 1 hr, then the mixture is evaporated using a rotary evaporator. The resulting residue is dissolved in a solvent (such as DCM and the like) and treated with a base (such as 1N NaOH or 1N KOH and the like) to about pH 14. The organic layer is dried (such as over $K_2CO_3$) and evaporated to provide the substituted 4-phenyl-piperidine Compound A5, which is used in the next step without further purification. The Compound A5 may also be commercially available.

Compound A5, a $R_5$ substituted (4-oxo-cyclohexyl)-carbamic acid tert-butyl ester Compound A6, a reducing agent (such as $NaBH(OAc)_3$ and the like), with or without a catalytic amount of an acid (such as HOAc and the like) and a dry solvent (such as anhydrous DCM and the like) are mixed together at r.t. to form a slurry. The mixture is stirred under a nitrogen atmosphere until Compound A6 is no longer detected (using TLC and/or LCMS). The mixture is diluted with a solvent (such as AcOEt and the like), sequentially washed (with water, $NaHCO_3$ or $NH_4Cl$ (saturated) and the like) and dried (such as over $Na_2SO_4$). The filtered dry solution is evaporated using a rotary evaporator to produce a residue, which is purified via flash chromatography to provide Compound A7 as a mixture (represented by wave bond lines) of cis and trans isomers.

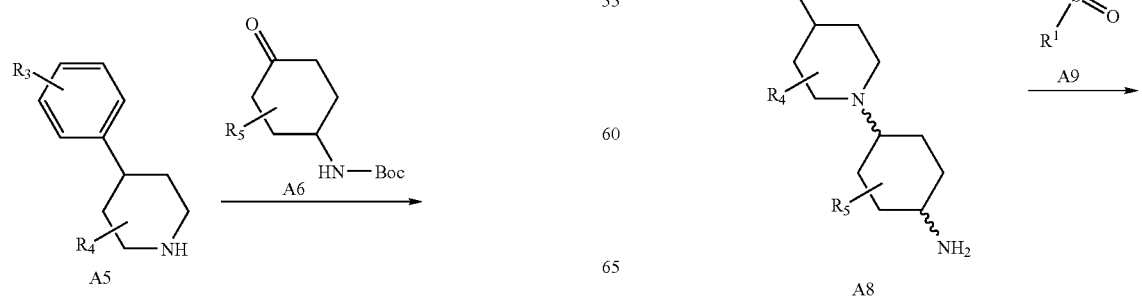

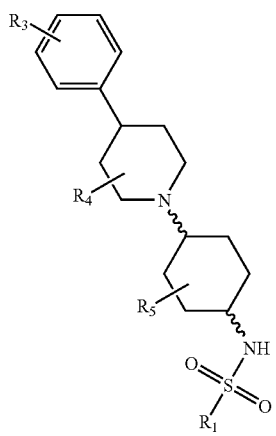

A10

Compound A7 is dissolved in a solvent (such as DCM and the like) at r.t., then stirred into an acid (such as TFA and the like). The mixture is stirred for a period of from about 30 mins. to about 1.5 hrs, then evaporated using a rotary evaporator to produce a residue which is mixed with a solvent (such as DCM and the like), then treated with a base (such as 1N NaOH or 1N KOH and the like) to about pH 14. The aqueous layer is separated and extracted (using a solvent such as DCM and the like) and the combined organic extracts are dried (such as over $K_2CO_3$ or $Na_2SO_4$ and the like) to provide Compound A8 as a crude product, which is used in the next step without further purification.

Compound A8 and an $R_1$ substituted sulfonyl chloride Compound A9 are dissolved in a solvent (such as DCM and the like). A mild base such as $K_2CO_3$ is added to form a yellowish turbid solution. The solution is stirred at r.t. until Compound A8 is no longer detected (using TLC and/or LCMS). The mixture is filtered to provide a solution of Compound A10 as a cis and trans isomer mixture.

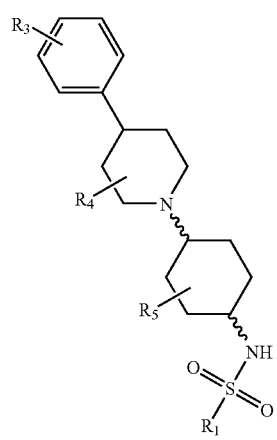

A10

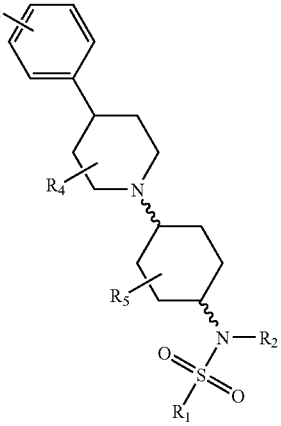

A11

The substituents for Compound A7, Compound A8 or Compound A10 may be further substituted either before or after deprotection using various reaction materials, reagent(s) and conditions, thus enabling the preparation of other compounds that are representative of the invention by one skilled in the art. For example, the Compound A10 NH portion of —$NHSO_2$—$R_1$ may be further substituted by an alkylation or another similar substitution reaction with an $R_2$ substituent having an amenable reaction group to provide Compound A11.

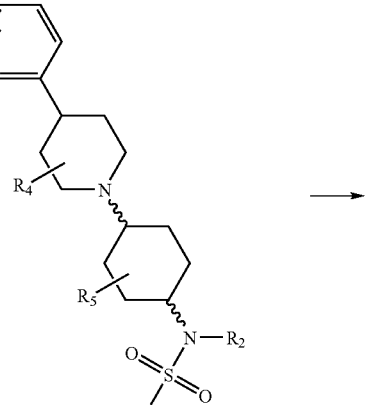

A11

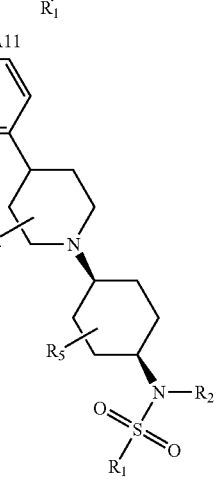

A12

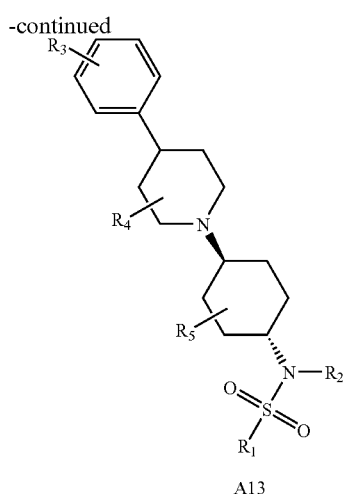

A13

The Compound A11 isomers, i.e., Compound A12 and Compound A13 are separated via chromatographic techniques such as preparative TLC (using an eluent mixture such as 5% MeOH/DCM and the like). A cis isomer such as Compound A11 is less polar and a trans isomer such as Compound A12 is polar.

EXAMPLE 1

N-cis-{4-[4-(2-isopropoxy-phenyl)-piperidin-1-yl]-cyclohexyl}-3,4-dimethoxy-benzenesulfonamide (Cpd 1)

N-trans-{4-[4-(2-isopropoxy-phenyl)-piperidin-1-yl]-cyclohexyl}-3,4-dimethoxy-benzenesulfonamide (Cpd 2)

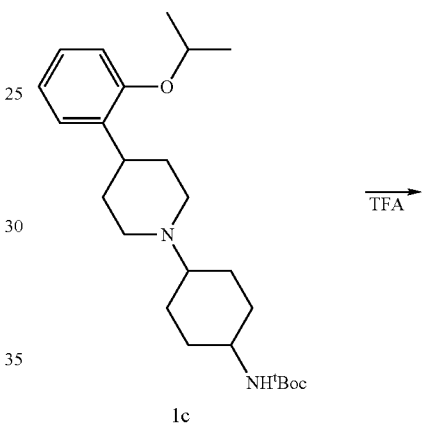

A (4-oxo-cyclohexyl)-carbamic acid tert-butyl ester Compound 1b (1.54 g, 7.21 mmol), NaBH(OAc)$_3$ (64.45 g, 21.0 mmol) and HOAc (0.3 mL) were added to a solution of 4-(2-isopropoxy-phenyl)-piperidine Compound 1a (1.32 g, 6.01 mmol) in CH$_2$Cl$_2$ (100 mL). The mixture was stirred under N$_2$ for two days, then the reaction was quenched with MeOH. The mixture was evaporated and the resulting residue was redissolved with CH$_2$Cl$_2$, washed using 10% aqueous Na$_2$CO$_3$ and brine, then dried (Na$_2$SO$_4$). The crude product was purified by column chromatography to provide {4-[4-(2-isopropoxy-phenyl)-piperidin-1-yl]-cyclohexyl}-carbamic acid tert-butyl ester Compound 1c as a mixture of cis/trans isomers (MS 416; yellowish oil; 1.19 g, 48% yield).

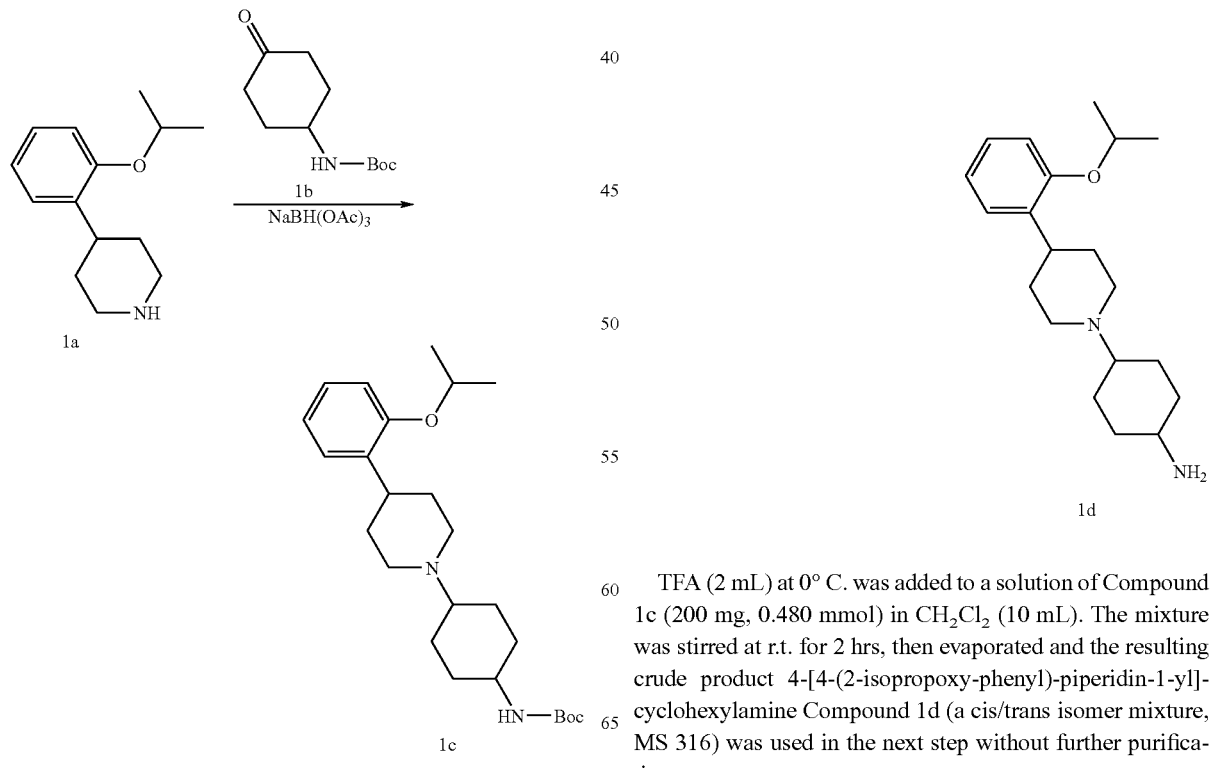

TFA (2 mL) at 0° C. was added to a solution of Compound 1c (200 mg, 0.480 mmol) in CH$_2$Cl$_2$ (10 mL). The mixture was stirred at r.t. for 2 hrs, then evaporated and the resulting crude product 4-[4-(2-isopropoxy-phenyl)-piperidin-1-yl]-cyclohexylamine Compound 1d (a cis/trans isomer mixture, MS 316) was used in the next step without further purification.

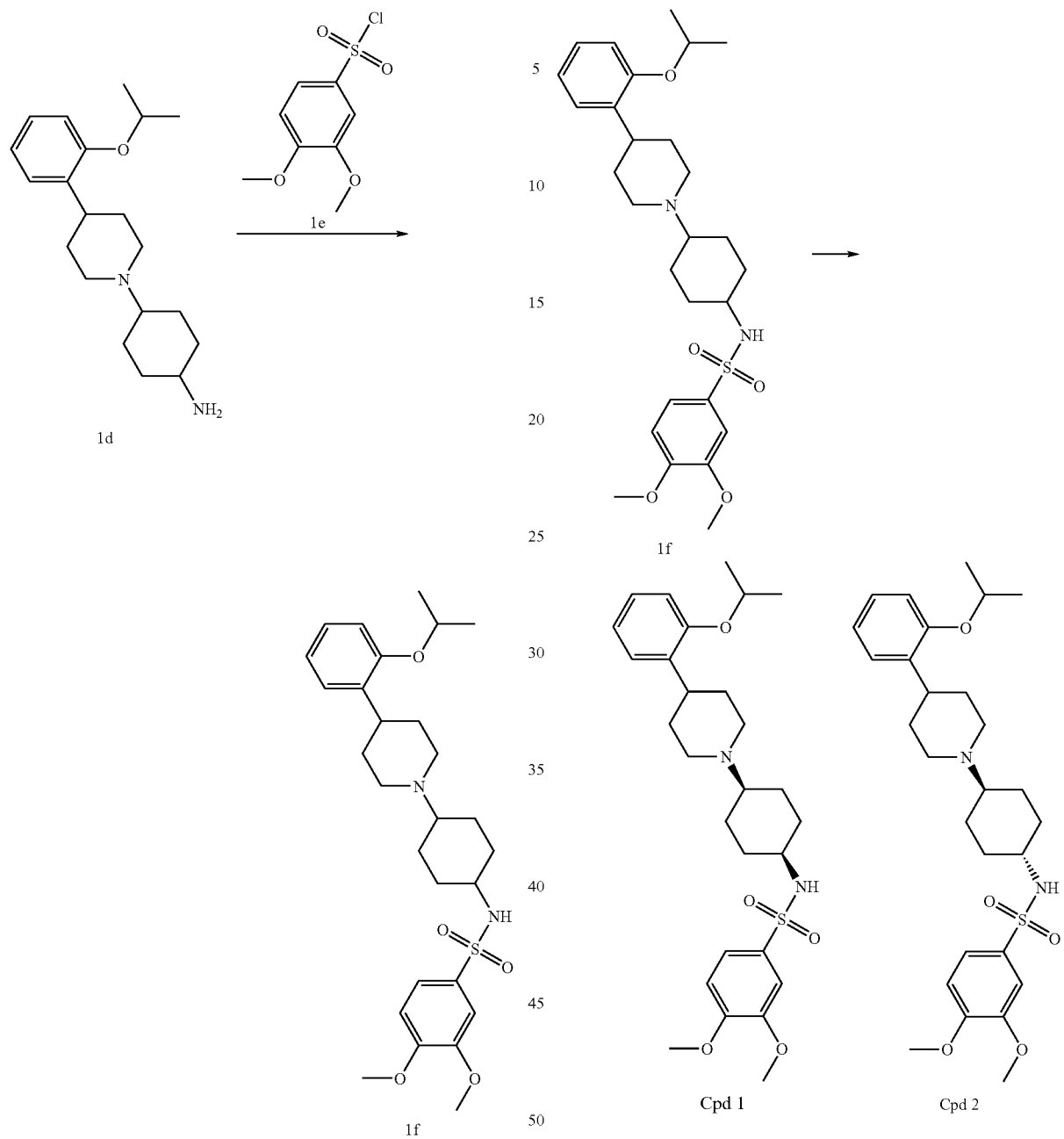

The 3,4-dimethoxy-benzenesulfonyl chloride Compound 1e (113 mg, 0.480 mmol) and an aqueous solution of 10% Na$_2$CO$_3$ (10 mL) were added to a solution of Compound 1d in CH$_2$Cl$_2$ (25 mL). The mixture was stirred at r.t. overnight. The organic layer was separated and dried (Na$_2$SO$_4$), then evaporated to provide N-{4-[4-(2-isopropoxy-phenyl)-piperidin-1-yl]-cyclohexyl}-3,4-dimethoxy-benzenesulfonamide Compound 1f as a cis/trans isomer mixture.

The Compound 1f mixture was separated via preparative TLC to provide Compound 1 (MS 516, M.P. 221° C., 59 mg, 24%) and Compound 2 (MS 516, M.P. 208° C., 138 mg, 56%), which were each converted to a fumarate salt.

Compound 1: $^1$H NMR (CDCl$_3$, TMS) δ 1.35 (d, J=6.5 Hz, 6H), 1.4~1.9 (m, 12H), 2.26 (m, 3H), 2.95 (m, 3H), 3.44 (bs, 1H), 3.95 (s, 3H), 3.97 (s, 3H), 4.54 (m, 1H), 5.07 (bd, J=10.5 Hz, 1H), 6.7~7.6 (m, 7H).

Compound 2: $^1$H NMR (CDCl$_3$, TMS) δ 1.1~1.4 (m, 4H), 1.32 (d, J=6.5 Hz, 6H), 1.66 (m, 2H), 1.92 (m, 6H), 2.30 (m, 3H), 2.94 (m, 4H), 3.92 (s, 3H), 3.98 (s, 3H), 4.52 (m, 1H), 4.60 (bd, J=9.0 Hz, 1H), 6.7~7.6 (m, 7H).

EXAMPLE 2

N-cis-{4-[4-(2-cyclopropoxy-phenyl)-piperidin-1-yl]-cyclohexyl}-3,4-dimethoxy-benzenesulfonamide (Cpd 7)

N-trans-{4-[4-(2-cyclopropoxy-phenyl)-piperidin-1-yl]-cyclohexyl}-3,4-dimethoxy-benzenesulfonamide (Cpd 8)

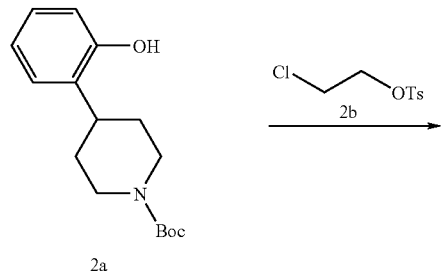

-continued

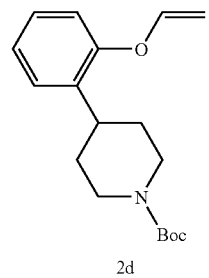

Compound 2c (0.78 g, 2.3 mmol) was dissolved into dry THF (20 mL) and cooled to 0° C. The solution was stirred and tert-BuOK (1.03 g, 9.2 mmol) was added. The resulting yellow clear solution was stirred at 0° C. for 0.5 hr, and then at r.t. for 2 hrs. TLC (using 25% AcOEt/hexane as eluent) confirmed that the reaction was complete. The solution was cooled to 0° C., water (10 mL) was added and the excess THF was removed on a rotary evaporator. The remaining aqueous solution was extracted by AcOEt and dried over Na₂SO₄ to provide 4-(2-vinyloxy-phenyl)-piperidine-1-carboxylic acid tert-butyl ester Compound 2d as a colorless oil. LC-MS (3.863 min.) m/z 326.1 (M+Na⁺).

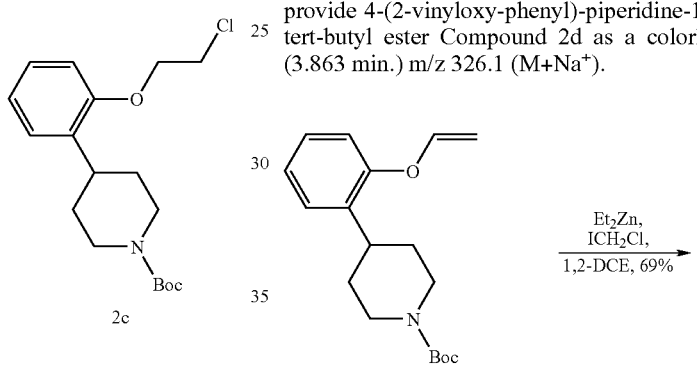

A solution of 4-(2-hydroxy-phenyl)-piperidine-1-carboxylic acid tert-butyl ester Compound 2a (0.67 g, 2.42 mmol), toluene-4-sulfonic acid 2-chloro-ethyl ester Compound 2b (1.13 g, 4.84 mmol), Cs₂CO₃ (1.60 g, 4.84 mmol) and DMF (20 mL) were heated and stirred at 50° C. overnight (18 hrs). The excess DMF was removed under reduced pressure and the white residue was mixed with AcOEt (100 mL), washed with water and dried over Na₂SO₄. The filtered dry solution was evaporated and the product was purified via flash chromatography (silica gel, 25% AcOEt/hexane) to provide 4-[2-(2-chloro-ethoxy)-phenyl]-piperidine-1-carboxylic acid tert-butyl ester Compound 2c (0.78 g, 95%) as a colorless sticky oil. LC-MS (3.943 min.) m/z 362.1 (M+Na⁺).

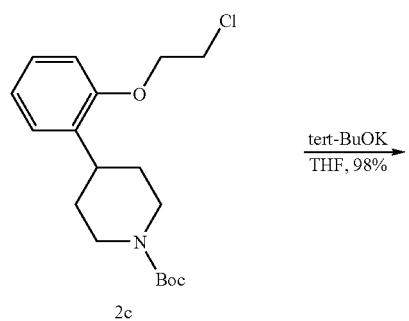

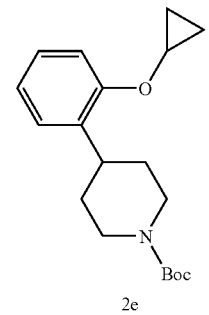

1,2-Dichloroethane (DCE)(20 mL) was cooled to −40° C. and stirred. ZnEt₂ (14 mL, 1.0 M hexane) was added with stirring into the solution. The mixture was stirred until white smoke was no longer produced. A solution of Compound 2d in DCE (30 mL) was added and stirred for a few minutes until the solution became almost colorless and clear. Chloro-iodo-methane (ICH₂Cl) (1.63 mL, 22 mmol) was added dropwise and the mixture was stirred for 8 hrs as the temperature went from −40° C. to −15° C. The white turbid mixture was diluted with AcOEt (100 mL), cooled to −40° C. and NH₄Cl (saturated, 30 mL) was added. The two layers were separated and the organic extracts were dried over Na₂SO₄. The filtered dry solution was evaporated and the product was purified via flash chromatography (silica gel, 10% AcOEt/hexane) to provide 4-(2-cyclopropoxy-phenyl)-piperidine-1-carboxylic acid tert-butyl ester Compound 2e (0.488 g, 68.6%). LC-MS (4.291 min.) m/z 262.2 (M+H$^{+1-56}$).

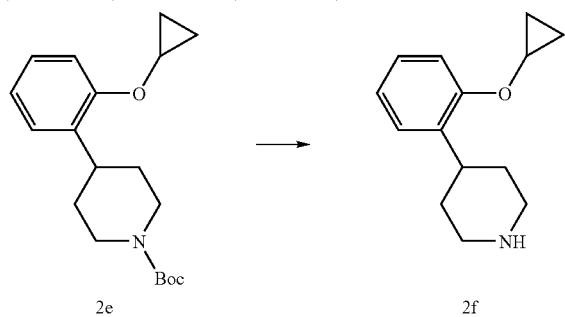

Compound 2e (0.48 g, 1.5 mmol) was dissolved into DCM and stirred with TFA and a catalytic amount of water at r.t. for 1 hr. The mixture was evaporated using a rotary evaporator to produce a residue which was mixed with DCM and treated with 1N NaOH to pH ~14. The organic layer was dried over K$_2$CO$_3$ and evaporated to provide 4-(2-cyclopropoxy-phenyl)-piperidine Compound 2f (0.233 g) as a yellowish oil, which was used in the next step without further purification.

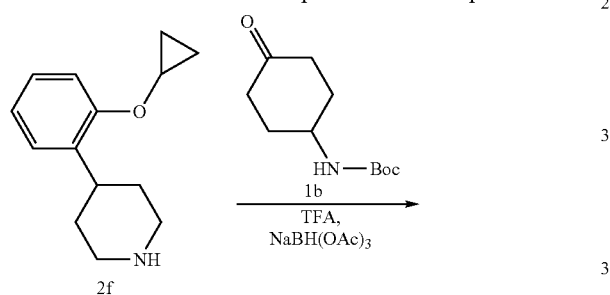

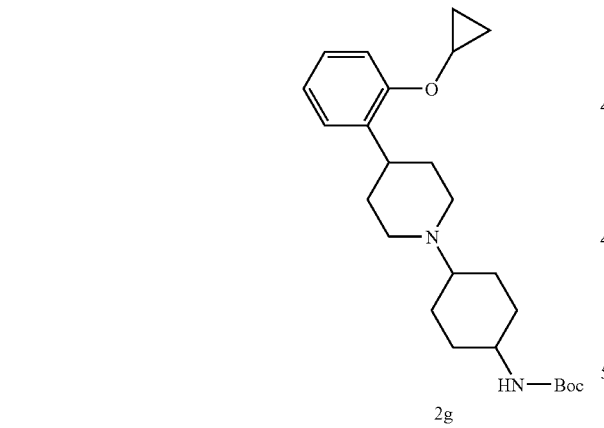

Compound 2f (0.233 g, 1.1 mmol), 4-oxo-piperidine-1-carboxylic acid tert-butyl ester Compound 1b (0.26 g, 1.2 mmol), NaBH(OAc)$_3$ (0.70 g, 3.4 mmol), HOAc (2 drops) and anhydrous DCM (30 mL) were added together. The mixture formed a white slurry and was stirred under a nitrogen atmosphere until the slurry turned to a yellowish solution. TLC confirmed that the reaction was complete. The mixture was diluted with AcOEt (80 mL), sequentially washed with NH$_4$Cl (saturated), 1 N NaOH and water, and dried over Na$_2$SO$_4$. The filtered dry solution was evaporated using a rotary evaporator to produce a residue which was purified via flash chromatography (silica gel, 100% AcOEt) to provide {4-[4-(2-cyclopropoxy-phenyl)-piperidin-1-yl]-cyclo-hexyl}-carbamic acid tert-butyl ester Compound 2g (0.325 g, yield 71%) as white sticky oil. LC-MS (2.863 min.) m/z 415.2 (M+H$^+$).

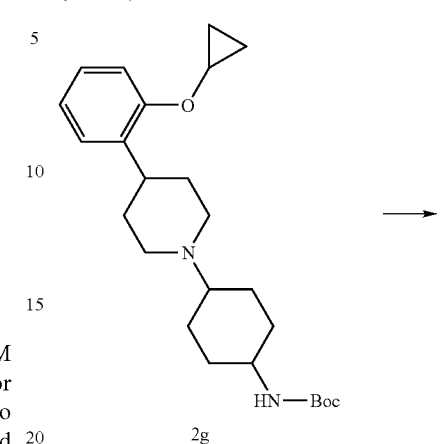

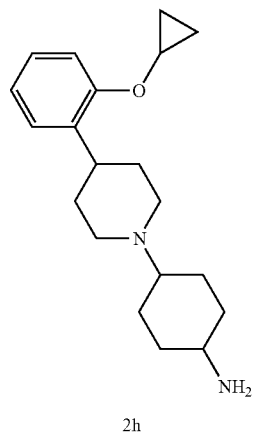

TFA (0.5 mL) was added to a solution of Compound 2g in DCM and the mixture was stirred at r.t. for 0.5 hrs. The mixture was evaporated using a rotary evaporator to produce a residue which was mixed with DCM and treated with 1N NaOH to pH ~14. The organic layer was dried over K$_2$CO$_3$ and evaporated to provide 4-[4-(2-cyclopropoxy-phenyl)-piperidin-1-yl]-cyclohexylamine Compound 2h (0.234 g, 99.6%) as a colorless sticky oil, which was used in the next step without further purification. LC-MS (2.356 min.), m/z 315.1 (M+H$^+$).

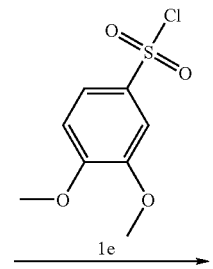

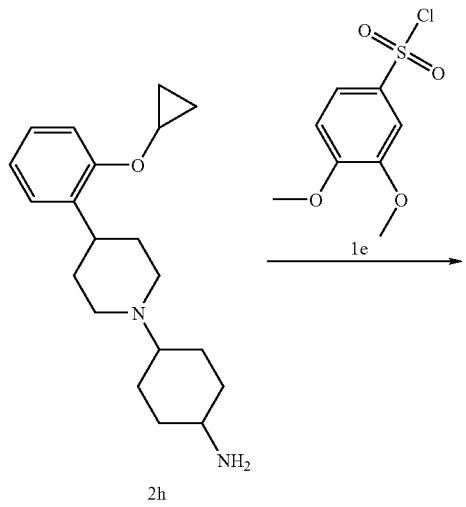

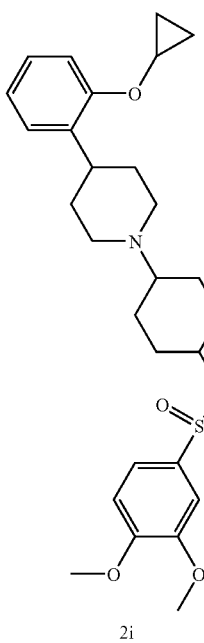

2i

Compound 2h (0.030 g, 0.096 mmol) and 3,4-dimethoxy-benzenesulfonyl chloride Compound 1e (0.034 g, 0.143 mmol) were dissolved into DCM (3 mL). The mixture formed a yellowish solution and K$_2$CO$_3$ (0.040 g) was added to form a yellowish turbid solution. The solution was stirred at r.t. until TLC (5% MeOH/DCM) and LC-MS confirmed that the reaction was complete, then filtered to provide a solution of N-{4-[4-(2-cyclopropoxy-phenyl)-piperidin-1-yl]-cyclohexyl}-3,4-dimethoxy-benzenesulfonamide Compound 2i as a cis/trans isomer mixture.

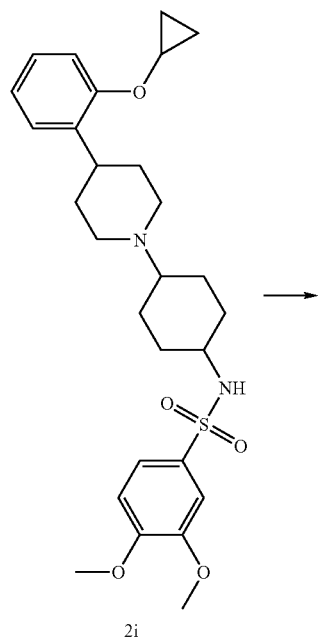

2i

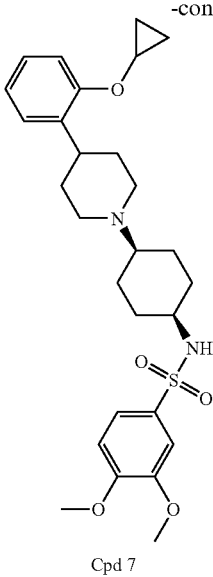

Cpd 7

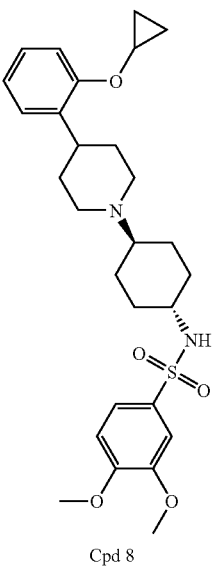

Cpd 8

The Compound 2i solution was filtered and the isomers were separated via preparative TLC (using the eluent mixture 5% MeOH/DCM).

A cis isomer Compound 7 (from the less polar TLC spot) was isolated (0.023 g) as a yellowish oil. LC-MS (2.990 min.) m/z 515.1 (100, M+H$^+$); $^1$H NMR (CDCl$_3$, TMS) δ 0.65-0.85 (m, 4H), 1.10-1.35 (m, 2H), 1.35-1.84 (m, 10H), 2.22-2.42 (m, 3H), 2.78-2.92 (m, 1H), 3.05 (d, J=11.2 Hz, 2H), 3.38-3.53 (m, 1H), 3.68-3.80 (m, 2H), 3.94 (s) & 3.96 (s, 6H), 6.88-7.00 (m, 2H), 7.12-7.26 (m, 3H), 7.41 (d, J=2.0 Hz, 1H), 7.53 (dd, J$_1$=2.0 Hz, J$_2$=8.4 Hz, 1H).

A trans isomer Compound 8 (from the polar TLC spot) was isolated (0.012 g) as a yellowish oil. LC-MS (2.763 min.) m/z 515.1 (100, M+H$^+$); $^1$H NMR (CDCl$_3$, TMS), δ 0.65-0.82 (m, 4H), 1.19-1.50 (m, 5H), 1.75-2.15 (m, 7H), 2.35-2.70 (m, 3H), 2.82-2.98 (m, 1H), 2.98-3.30 (m, 3H), 3.65-3.79 (m, 2H), 3.92 (s) & 3.96 (s, 6H), 6.80-7.00 (m, 2H), 7.07-7.25 (m, 3H), 7.37 (d, J=2.4 Hz, 1H), 7.50 (dd, J$_1$=2.4 Hz, J$_2$=8.6 Hz, 1H).

Following the procedure of Example 2, substituting the appropriate starting materials, reagents and solvents, the following compounds were prepared:

| Cpd | Name | MS | Ret. |
|---|---|---|---|
| 9 | 5-chloro-N-cis-{4-[4-(2-cyclopropoxy-phenyl)-piperidin-1-yl]-cyclohexyl}-2-methoxy-benzenesulfonamide | 519 | 2.998 |
| 10 | 5-chloro-N-trans-{4-[4-(2-cyclopropoxy-phenyl)-piperidin-1-yl]-cyclohexyl}-2-methoxy-benzenesulfonamide | 519 | 2.97 |
| 11 | 5-chloro-N-cis-{4-[4-(2-cyclopropoxy-phenyl)-piperidin-1-yl]-cyclohexyl}-2-fluoro-benzenesulfonamide | 507 | 3.008 |
| 12 | 5-chloro-N-trans-{4-[4-(2-cyclopropoxy-phenyl)-piperidin-1-yl]-cyclohexyl}-2-fluoro-benzenesulfonamide | 507 | 3.18 |
| 15 | 2,4-dichloro-N-cis-{4-[4-(2-cyclopropoxy-phenyl)-piperidin-1-yl]-cyclohexyl}-benzenesulfonamide | 523 | 3.099 |
| 16 | 2,4-dichloro-N-trans-{4-[4-(2-cyclopropoxy-phenyl)-piperidin-1-yl]-cyclohexyl}-benzenesulfonamide | 523 | 3.088 |

-continued

| Cpd | Name | MS | Ret. |
|---|---|---|---|
| 21 | benzo[1,3]dioxole-5-sulfonic acid cis-{4-[4-(2-cyclopropoxy-phenyl)-piperidin-1-yl]-cyclohexyl}-amide | 499 | 2.843 |
| 22 | benzo[1,3]dioxole-5-sulfonic acid trans-{4-[4-(2-cyclopropoxy-phenyl)-piperidin-1-yl]-cyclohexyl}-amide | 499 | 2.825 |

EXAMPLE 3

3,4-dimethoxy-N-cis-(4-{4-[2-(2,2,2-trifluoro-ethoxy)-phenyl]-piperidin-1-yl}-cyclohexyl)-benzenesulfonamide (Cpd 5)

3,4-dimethoxy-N-trans-(4-{4-[2-(2,2,2-trifluoro-ethoxy)-phenyl]-piperidin-1-yl}-cyclohexyl)-benzenesulfonamide (Cpd 6)

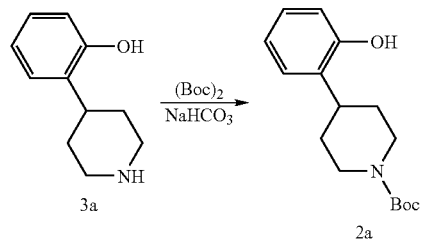

A solution of the hydrobromide salt of 2-piperidin-4-yl-phenol Compound 3a (5.00 g, 19.37 mmol) in water (400 mL) was made basic to pH 8 by the addition of NaHCO$_3$. A solution of O(Boc)$_2$ (4.22 g, 19.36 mmol) in THF (80 mL) was added and the mixture was stirred at r.t. over night. CH$_2$Cl$_2$ (500 mL) was added and the organic layer was isolated and dried. The crude product was purified by chromatography to provide 4-(2-hydroxy-phenyl)-piperidine-1-carboxylic acid tert-butyl ester Compound 2a (4.56 g, 85%) as a white powder $^1$H NMR δ 1.50 (s, 9H), 1.60 (m, 2H), 1.85 (bd, J=19.5 Hz, 2H), 2.82 (bm, 2H), 3.04 (m, 1H), 4.23 (bs, 2H), 6.7~7.2 (m, 4H).

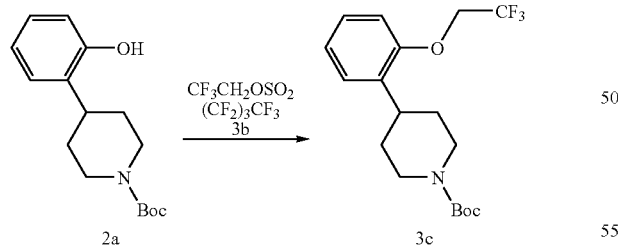

A suspension of Compound 2a (200 mg, 0.721 mmol), 1,1,2,2,3,3,4,4,4-nonafluoro-butane-1-sulfonic acid 2,2,2-trifluoro-ethyl ester Compound 3b (303 mg, 0.793 mmol) and Cs$_2$CO$_3$ (294 mg, 0.901 mmol) in DMF (15 mL) was heated to 50° C. for 2 hrs. The mixture was cooled to r.t. and diluted with AcOEt (100 mL), then washed ten times with water and dried. The product 4-[2-(2,2,2-trifluoro-ethoxy)-phenyl]-piperidine-1-carboxylic acid tert-butyl ester Compound 3c was obtained via short column chromatography (213 mg, 82.2%) as a sticky oil. MS 382 (M+Na); $^1$H NMR δ 1.48 (s, 9H), 1.58 (m, 2H), 1.78 (bd, J=13 Hz, 2H), 2.82 (bm, 2H), 3.12 (m, 1H), 4.25 (bs, 2H), 4.40 (q, J=11.7 Hz, 2H), 6.7~7.2 (m, 4H).

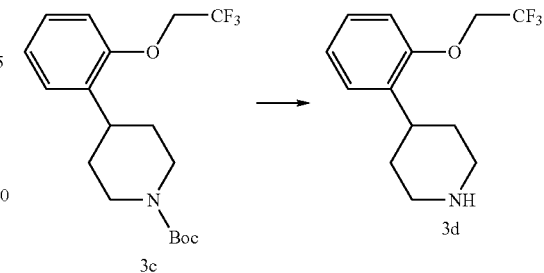

A solution of Compound 3c (267 mg, 0.742 mmol) in CH$_2$Cl$_2$ (5 mL) was treated with TFA (2 mL) at 0° C. over a period of 3 hrs. The mixture was evaporated and the resulting residue was redissolved with CH$_2$Cl$_2$ (50 mL), then washed using 10% Na$_2$CO$_3$ and dried. The dried solution was evaporated to provide 4-[4-(2-cyclopropoxy-phenyl)-piperidin-1-yl]-cyclohexylamine Compound 3d as a pale yellow oil, which was used in the next step without further purification (MS 259).

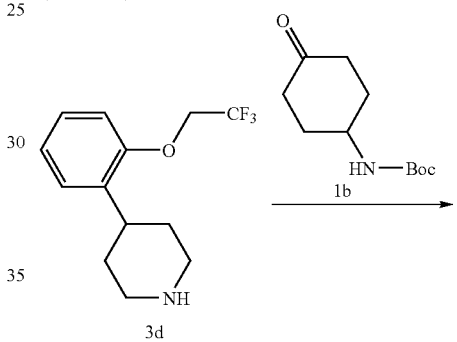

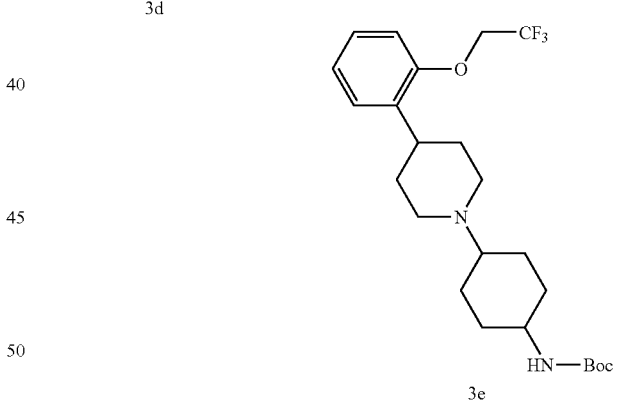

Ti[OCH(CH$_3$)$_2$]$_4$ (0.33 ml, 1.1 mmol) and 4-oxo-piperidine-1-carboxylic acid tert-butyl ester Compound 1b (158 mg, 0.74 mmol) were added to a solution of Compound 3d in CH$_2$Cl$_2$. The mixture was stirred at r.t. for 12 hrs, then NaBH$_4$ (220 mg, 5.81 mmol) was added. The mixture was stirred at r.t. for 16 hrs, then MeOH was added to quench the reaction. The mixture was evaporated and the resulting powder residue was extracted using CH$_2$Cl$_2$ and filtered. The solvent in the filtrate was evaporated and purified via chromatography to provide (4-{4-[2-(2,2,2-trifluoro-ethoxy)-phenyl]-piperidin-1-yl}-cyclohexyl)-carbamic acid tert-butyl ester Compound 3e (281 mg, 83%, white solid) as a cis/trans mixture of isomers (MS 456).

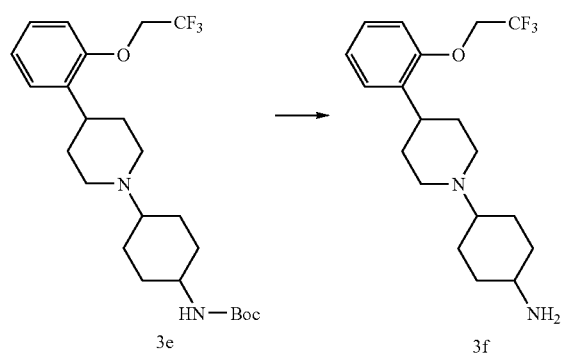

TFA (3 mL) at 0° C. was added to a solution of Compound 3e (262 mg, 0.573 mmol) in CH$_2$Cl$_2$ (10 mL). The mixture was stirred at r.t. for 2 hrs. The mixture was evaporated and the resulting crude 4-{4-[2-(2,2,2-trifluoro-ethoxy)-phenyl]-piperidin-1-yl}-cyclohexylamine Compound 3f was used in the next step without further purification.

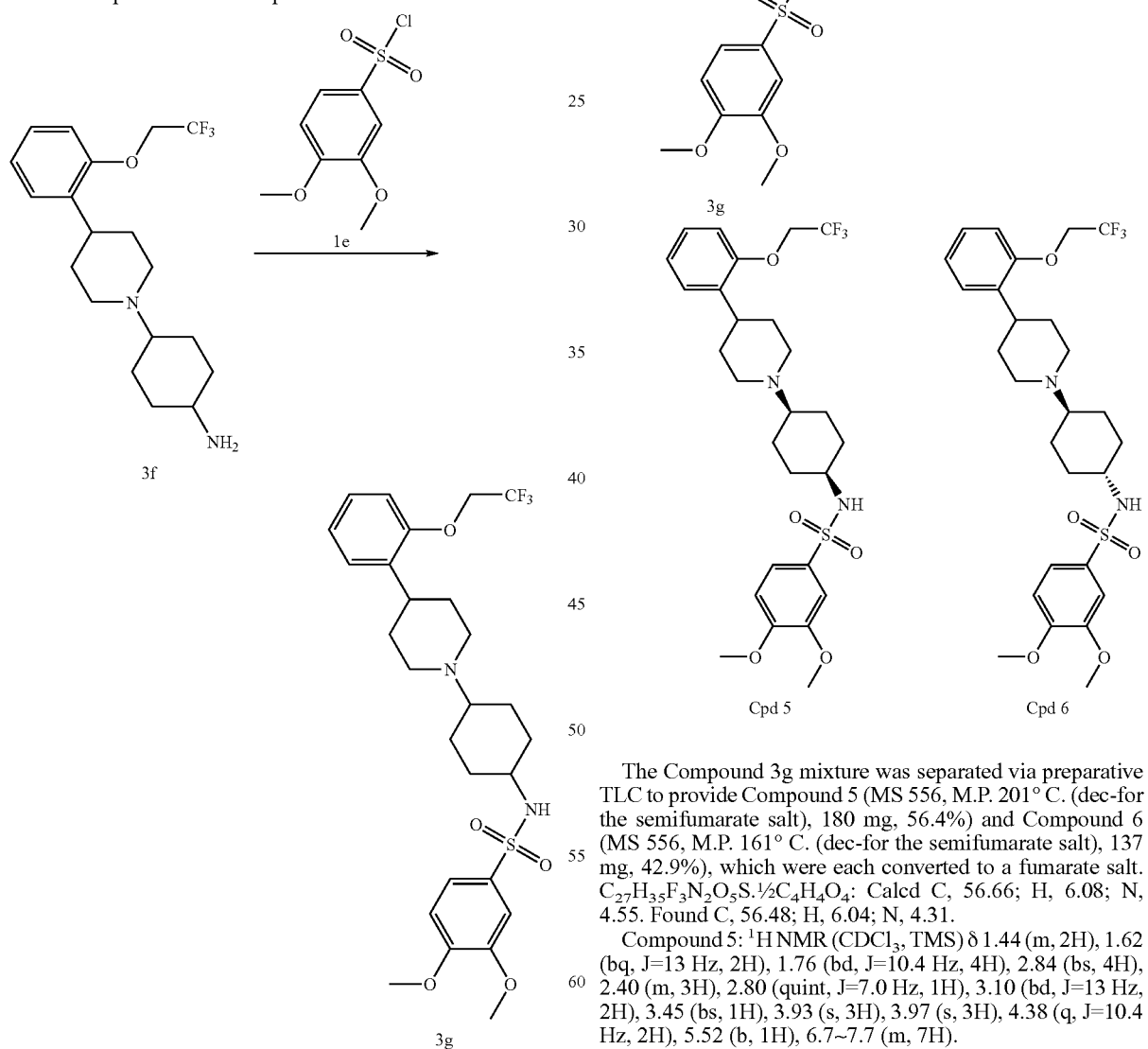

A 3,4-dimethoxy-benzenesulfonyl chloride Compound 1e (136 mg, 0.573 mmol) and an aqueous solution of 10% Na$_2$CO$_3$ (10 mL) were added to a solution of Compound 3f in CH$_2$Cl$_2$ (25 mL). The mixture was stirred at r.t. overnight. The organic layer was separated, dried (Na$_2$SO$_4$) and evaporated to provide 3,4-dimethoxy-N-(4-{4-[2-(2,2,2-trifluoro-ethoxy)-phenyl]-piperidin-1-yl}-cyclohexyl)-benzene-sulfonamide Compound 3g as a cis/trans isomer mixture.

The Compound 3g mixture was separated via preparative TLC to provide Compound 5 (MS 556, M.P. 201° C. (dec-for the semifumarate salt), 180 mg, 56.4%) and Compound 6 (MS 556, M.P. 161° C. (dec-for the semifumarate salt), 137 mg, 42.9%), which were each converted to a fumarate salt. C$_{27}$H$_{35}$F$_3$N$_2$O$_5$S·½C$_4$H$_4$O$_4$: Calcd C, 56.66; H, 6.08; N, 4.55. Found C, 56.48; H, 6.04; N, 4.31.

Compound 5: $^1$H NMR (CDCl$_3$, TMS) δ 1.44 (m, 2H), 1.62 (bq, J=13 Hz, 2H), 1.76 (bd, J=10.4 Hz, 4H), 2.84 (bs, 4H), 2.40 (m, 3H), 2.80 (quint, J=7.0 Hz, 1H), 3.10 (bd, J=13 Hz, 2H), 3.45 (bs, 1H), 3.93 (s, 3H), 3.97 (s, 3H), 4.38 (q, J=10.4 Hz, 2H), 5.52 (b, 1H), 6.7~7.7 (m, 7H).

Compound 6: $^1$H NMR (CDCl$_3$, TMS) δ 1.20 (bq, J=12 Hz, 2H), 1.33 (bq, J=13 Hz, 2H), 1.6~1.9 (m, 4H), 1.92 (bd, J=11.7 Hz, 4H), 2.35 (bt, J=13 Hz, 3H), 3.02 (m, 4H), 3.95 (s, 3H), 3.97 (s, 3H), 4.35 (q, J=14.3 Hz, 2H), 4.54 (bd, J=10 Hz, 1H), 6.7~7.6 (m, 7H).

Following the procedure of Example 3, substituting the appropriate starting materials, reagents and solvents, the following compounds were prepared (MS units: m/z M+H⁺; M.P. units: ° C. for the fumarate salt):

| Cpd | Name | MS | M.P. |
|---|---|---|---|
| 3 | 3,4-difluoro-N-cis-{4-[4-(2-isopropoxy-phenyl)-piperidin-1-yl]-cyclohexyl}-benzenesulfonamide | 492 | 176 |
| 4 | 3,4-difluoro-N-trans-{4-[4-(2-isopropoxy-phenyl)-piperidin-1-yl]-cyclohexyl}-benzenesulfonamide | 492 | 239 |
| 13 | 2,3-dihydro-benzo[1,4]dioxine-6-sulfonic acid cis-(4-{4-[2-(2,2,2-trifluoro-ethoxy)-phenyl]-piperidin-1-yl}-cyclohexyl)-amide | 554 | 190 |
| 14 | 2,3-dihydro-benzo[1,4]dioxine-6-sulfonic acid trans-(4-{4-[2-(2,2,2-trifluoro-ethoxy)-phenyl]-piperidin-1-yl}-cyclohexyl)-amide | 554 | 146 |
| 17 | 5-chloro-2-methoxy-N-cis-(4-{4-[2-(2,2,2-trifluoro-ethoxy)-phenyl]-piperidin-1-yl}-cyclohexyl)-benzenesulfonamide | 561 | 200 |
| 18 | 5-chloro-2-methoxy-N-trans-(4-{4-[2-(2,2,2-trifluoro-ethoxy)-phenyl]-piperidin-1-yl}-cyclohexyl)-benzenesulfonamide | 561 | 197 |
| 19 | 5-chloro-2-fluoro-N-cis-(4-{4-[2-(2,2,2-trifluoro-ethoxy)-phenyl]-piperidin-1-yl}-cyclohexyl)-benzenesulfonamide | 549 | 204 |
| 20 | 5-chloro-2-fluoro-N-trans-(4-{4-[2-(2,2,2-trifluoro-ethoxy)-phenyl]-piperidin-1-yl}-cyclohexyl)-benzenesulfonamide | 549 | 227 |
| 23 | 3-difluoromethoxy-N-cis-(4-{4-[2-(2,2,2-trifluoro-ethoxy)-phenyl]-piperidin-1-yl}-cyclohexyl)-benzenesulfonamide | 562 | 105 |
| 24 | 3-difluoromethoxy-N-trans-(4-{4-[2-(2,2,2-trifluoro-ethoxy)-phenyl]-piperidin-1-yl}-cyclohexyl)-benzenesulfonamide | 562 | 169 |
| 25 | 4-difluoromethoxy-N-cis-(4-{4-[2-(2,2,2-trifluoro-ethoxy)-phenyl]-piperidin-1-yl}-cyclohexyl)-benzenesulfonamide | 562 | 196 |
| 26 | 4-difluoromethoxy-N-trans-(4-{4-[2-(2,2,2-trifluoro-ethoxy)-phenyl]-piperidin-1-yl}-cyclohexyl)-benzenesulfonamide | 562 | 155 |
| 27 | N-cis-(4-{4-[2-(2-fluoro-ethoxy)-phenyl]-piperidin-1-yl}-cyclohexyl)-3,4-dimethoxy-benzenesulfonamide | 520 | 225 |
| 28 | N-trans-(4-{4-[2-(2-fluoro-ethoxy)-phenyl]-piperidin-1-yl}-cyclohexyl)-3,4-dimethoxy-benzenesulfonamide | 520 | 142 |
| 29 | N-cis-(4-{4-[2-(2,2-difluoro-ethoxy)-phenyl]-piperidin-1-yl}-cyclohexyl)-3,4-dimethoxy-benzenesulfonamide | 538 | 219 |
| 30 | N-trans-(4-{4-[2-(2,2-difluoro-ethoxy)-phenyl]-piperidin-1-yl}-cyclohexyl)-3,4-dimethoxy-benzenesulfonamide | 538 | 197 |

EXAMPLE 4

N-cis-{4-[4-(4-fluoro-2-isopropoxy-phenyl)-piperidin-1-yl]-cyclohexyl}-3,4-dimethoxy-benzenesulfonamide (Cpd 31)

N-trans-{4-[4-(4-fluoro-2-isopropoxy-phenyl)-piperidin-1-yl]-cyclohexyl}-3,4-dimethoxy-benzenesulfonamide (Cpd 32)

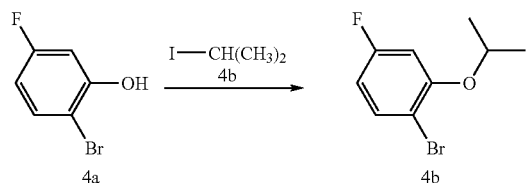

2-Bromo-5-fluoro-phenol Compound 4a (3.0 g, 15.7 mmol), 2-iodo-propane Compound 4b (4.0 g, 23.6 mmol), K₂CO₃ (3.3 g, 23.6 mmol) and DMF (50 mL) were heated and stirred at 80° C. for 8 hrs. The excess DMF was removed under reduced pressure and the white residue was mixed with AcOEt (100 mL), washed with water and dried (Na₂SO₄). The filtered dry solution was evaporated to provide 1-bromo-4-fluoro-2-isopropoxy-benzene Compound 4c (3.48 g, 95%) as a yellowish oil.

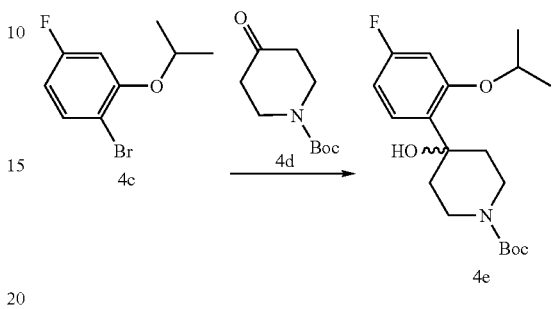

Compound 4c (0.75 g, 3.2 mmol) was dissolved into dry THF (10 mL) and cooled to −78° C. The colorless clear solution was treated with n-BuLi (1.3 mL, 2.5 M, 3.2 mmol) at −78° C. over a period of 15 mins. A solution of 4-oxo-piperidine-1-carboxylic acid tert-butyl ester Compound 4d (0.96 g, 4.8 mmol) in THF was added and the yellowish mixture was stirred at −78° C.-rt for 5 hrs. The reaction was quenched with NH₄Cl (saturated, 5 mL). The layers were separated and the organic extracts were dried. The filtered dry solution was evaporated and a crude product was obtained (1.515 g) as a yellowish oil. The product was purified via flash chromatography (silica gel, 10% AcOEt/hexane) to provide 4-(4-fluoro-2-isopropoxy-phenyl)-4-hydroxy-piperidine-1-carboxylic acid tert-butyl ester Compound 4e (0.858 g, 76%) as a colorless sticky oil.

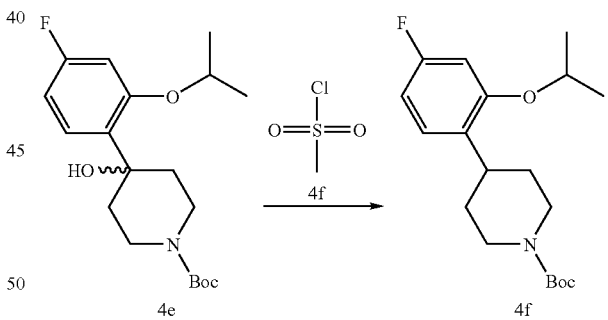

Compound 4e (0.855 g, 2.43 mmol) was dissolved into dry DCM (40 mL) and cooled to −78° C. The colorless solution was treated with methanesulfonyl chloride (0.42 g, 3.64 mmol) over a period of 30 mins followed by Et₃N (0.37 g, 3.64 mmol). The reaction mixture was warmed to r.t. gradually and quenched. The layers were separated and the organic extracts were dried. The filtered dry solution was evaporated and a crude product was obtained as a yellow oil. The product was purified via flash chromatography (silica gel, 10% AcOEt/hexane) to provide 4-(4-fluoro-2-isopropoxy-phenyl)-piperidine-1-carboxylic acid tert-butyl ester Compound 4f (0.52 g, 64%) as a colorless oil.

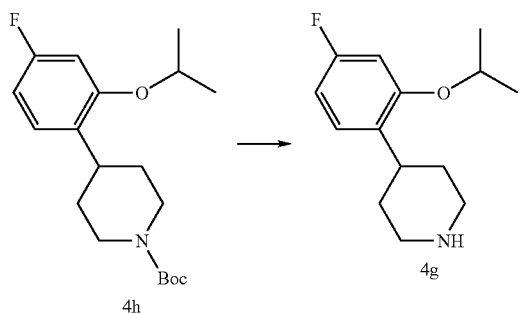

Compound 4f (1.10 g, 3.3 mmol) was dissolved into EtOH (100%, 50 mL) and 10% Pt/carbon (0.5 g) and HOAc (2 drops) were added. The mixture was shaken under H₂ (50 psi) at r.t. for 18 hrs and filtered through celite. Evaporation to dryness gave a piperidine intermediate (1.03 g, 93%) as a colorless solid. The piperidine intermediate (0.34 g, 1 mmol) was dissolved into DCM (5 mL) and the solution was treated with TFA (1 mL) at r.t. over a period of 1 hr. The mixture was evaporated using a rotary evaporator to produce a residue which was mixed with DCM and treated with 1N NaOH to pH ~14. The organic layer was dried over K₂CO₃ and evaporated to provide 4-(4-fluoro-2-isopropoxy-phenyl)-piperidine Compound 4g (0.3 g) as a colorless oil, which was used in the next step without further purification.

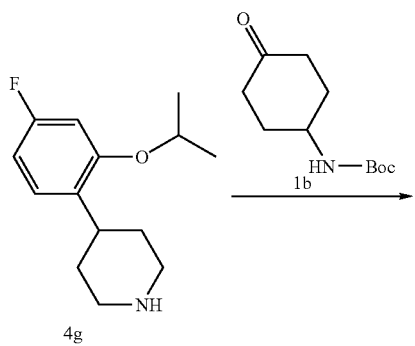

Compound 4g (0.3 g, 1.3 mmol), (4-oxo-cyclohexyl)-carbamic acid tert-butyl ester Compound 1b (0.32 g, 1.5 mmol), NaBH(OAc)₃ (0.74 g, 3.5 mmol), HOAc (2 drops) and anhydrous DCM (20 mL) were added together. The mixture formed a white slurry and was stirred under a nitrogen atmosphere until the slurry turned to a yellowish solution. TLC confirmed that the reaction was complete. The mixture was diluted with AcOEt (80 mL), sequentially washed with NaHCO₃ and NH₄Cl (saturated) and dried over Na₂SO₄. The filtered dry solution was evaporated using a rotary evaporator to produce a residue which was purified via flash chromatography (silica gel, 100% AcOEt) to provide {4-[4-(4-fluoro-2-isopropoxy-phenyl)-piperidin-1-yl]-cyclohexyl}-carbamic acid tert-butyl ester Compound 4h (0.18 g, 32%) as a colorless oil. LC-MS (3.245 min.) m/z 435.3 (M+H⁺).

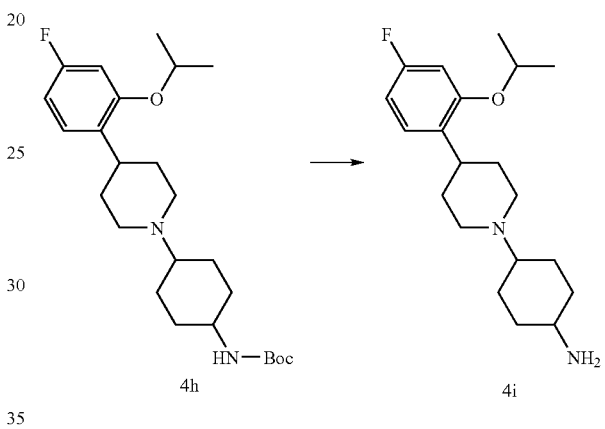

Compound 4h (0.18 g) was dissolved into DCM and TFA (0.1 mL) was added. The mixture was stirred at r.t. for 1.5 hrs, then evaporated using a rotary evaporator to produce a residue which was mixed with DCM and treated with 1N KOH to pH ~14. The organic layer was dried over K₂CO₃ and evaporated to provide 4-[4-(4-fluoro-2-isopropoxy-phenyl)-piperidin-1-yl]-cyclohexylamine Compound 4i (0.135 g, 97%) as a colorless oil, which was used in the next step without further purification. LC-MS (2.566 min.) m/z 335.2 (M+H⁺).

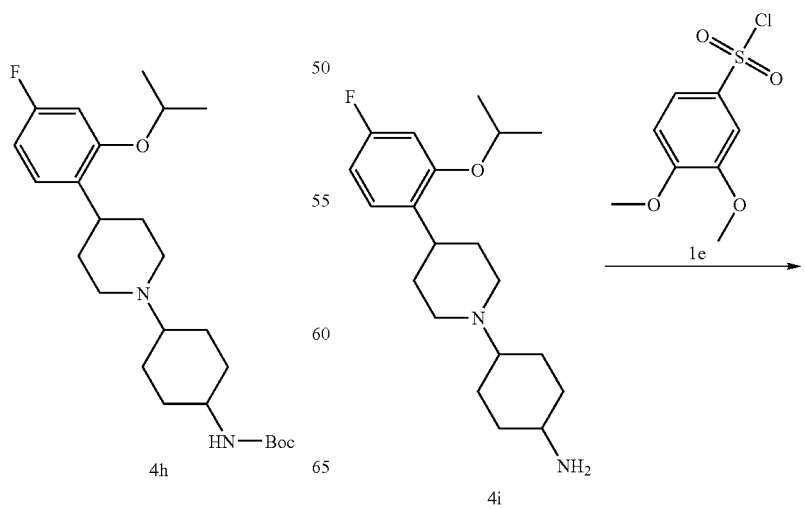

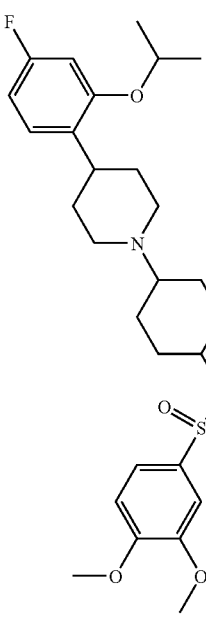

4j

Compound 4i (0.060 g, 0.18 mmol) and 3,4-dimethoxy-benzenesulfonyl chloride Compound 1e (0.064 g, 0.27 mmol) were dissolved into DCM (6 mL). The mixture formed a yellowish solution and $K_2CO_3$ (0.050 g) was added to form a yellowish turbid solution. The solution was stirred at r.t. until TLC (5% MeOH/DCM) and LC-MS confirmed that the reaction was complete, then filtered to provide a solution of N-{4-[4-(4-fluoro-2-isopropoxy-phenyl)-piperidin-1-yl]-cyclohexyl}-3,4-dimethoxy-benzenesulfonamide Compound 4j as a cis/trans isomer mixture.

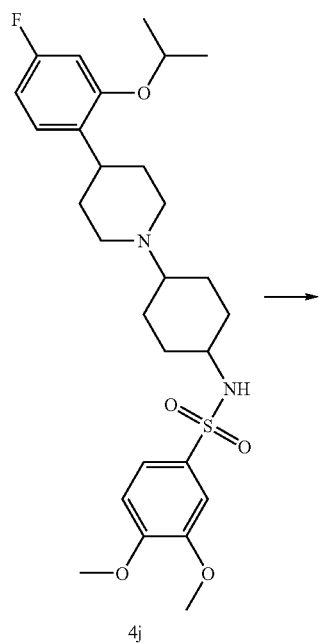

4j

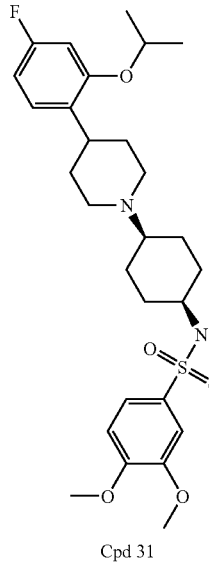

Cpd 31

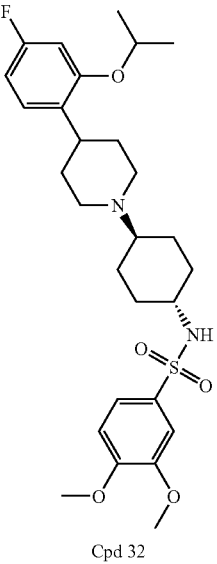

Cpd 32

The Compound 4j isomers were separated via preparative TLC (using the eluent mixture 5% MeOH/DCM).

A cis isomer Compound 31 (from the less polar TLC spot) was isolated (0.042 g, 88%) as a colorless oil. LC-MS (3.151 min.) m/z 535.2 (100, M+H$^+$); $^1$H NMR (CDCl$_3$, TMS) δ 1.38 (d, J=6.0 Hz, 6H), 1.42-1.98 (m, 12H), 2.20-2.45 (m, 3H), 2.82-2.98 (m, 1H), 2.98-3.25 (m, 2H), 3.40-3.54 (m, 1H), 3.97 (s) & 3.99 (s, 6H), 4.40-4.65 (m, 1H), 5.10-5.38 (m, 1H), 6.68-6.74 (m, 2H), 6.97 (d, J=8.8 Hz, 1H), 7.14 (t, J=7.2 Hz, 1H), 7.46 (d, J=2.4 Hz, 1H), 7.57 (dd, J$_1$=2.0 Hz, J$_2$=8.0 Hz, 1H).

A trans isomer Compound 32 (from the polar TLC spot) was isolated (0.028 g) as a colorless oil. LC-MS (2.931 min.) m/z 535.2 (100, M+H$^+$); $^1$H NMR (CDCl$_3$, TMS) δ 1.15-1.32 (m, 4H), 1.35 (d, J=6.4 Hz, 6H), 1.41-1.74 (m, 2H), 1.80 (d, J=12.4 Hz, 2H), 1.93 (t, J=12.4 Hz, 4H), 2.32 (t, J=10.8 Hz, 3H), 2.85 (t, J=12.0 Hz, 1H), 2.98 (d, J=10.8 Hz, 2H), 3.02-3.25 (m, 1H), 3.95 (s) & 3.98 (s, 6H), 4.42-4.60 (m, 1H), 4.60-4.80 (m, 1H), 6.50-6.70 (m, 2H), 6.96 (d, J=8.8 Hz, 1H), 7.11 (t, J=8.4 Hz, 1H), 7.39 (d, J=2.0 Hz, 1H), 7.52 (dd, J$_1$=2 Hz, J$_2$=8.6 Hz, 1H).

Following the procedure of Example 4, substituting the appropriate starting materials, reagents and solvents, the following compounds were prepared:

| Cpd | Name | MS | Ret. |
|-----|------|-----|------|
| 33 | N-cis-{4-[4-(5-fluoro-2-isopropoxy-phenyl)-piperidin-1-yl]-cyclohexyl}-3,4-dimethoxy-benzenesulfonamide | 535 | 3.151 |
| 34 | N-trans-{4-[4-(5-fluoro-2-isopropoxy-phenyl)-piperidin-1-yl]-cyclohexyl}-3,4-dimethoxy-benzenesulfonamide | 535 | 3.119 |

BIOLOGICAL EXAMPLES

α$_1$-Adrenergic Receptor Binding Assay

Preparation of COS Cell Membranes

Membranes were prepared from COS-7 cells (African Green monkey kidney SV40-transformed cells) that had been transfected with one of the three $\alpha_1$-AR subtypes (Genbank accession number for the $\alpha_{1a}$ subtype: AF013261; Genbank accession number for the $\alpha_{1b}$ subtype: NM000679; Genbank accession number for the $\alpha_{1d}$ subtype: NM000678) using the following method: COS cells from ten 100 mm tissue culture plates were scraped into a 5 mL volume of TE (a mixture of 50 mM Tris-HCl, 5 mM EDTA, pH 7.4). The cell suspension was disrupted with a Brinkman Polytron (at a setting of 8) for 10 sec. The disrupted cells were centrifuged at 1000×g for 10 min at 4° C. Supernatants were centrifuged at 34,500×g for 20 min at 4° C. The membrane pellets were suspended in a 2 mL volume of TNE (a mixture of 50 mM Tris-HCl, 5 mM EDTA and 150 mM NaCl at pH 7.4). An aliquot of the membrane suspension was stored at −70° C. until use. The protein concentration was determined using the BioRad "DC" protein assay kit following membrane solubilization with Triton X-100.

Radio-Ligand Binding Assay

Triplicate determinations of radio-ligand binding in the presence of increasing concentrations of testing compound were made. The reagents were added to 96-well polypropylene plate wells. Each assay well contained 140 µL TNE, 25 µL $^{125}$I-2-(β-4-hydroxyphenyl)ethylaminomethyltetralone ($^{125}$I-HEAT) (specific activity 2200 Ci/mmol, Dupont-New England Nuclear, 50 µM final), 10 µL testing compound dissolved in dimethyl sulfoxide (DMSO) (1 pM to 10 µM in half-log increments, final), and 25 µL appropriate $\alpha_1$-AR membrane subtype suspension in TNE (0.5 ng/µL for the $\alpha_{1a}$ and $\alpha_{1b}$ subtypes and 13 ng/µL for the $\alpha_{1d}$ subtype). The plate was incubated at rt for 1 hr. The contents of the wells were filtered through a glass filter (type C) (GF/C) membrane Unifilter plate (Packard Instruments) using the Packard Filtermate cell harvester. The filter plates were dried in a vacuum oven for 30 min at 40° C. 25 µL Microscint 20 liquid scintillation fluid (Packard Instuments) was added to each well. The radioactive content was analyzed in the TopCount microplate scintillation counter (Packard Instruments).

Data Analysis

The $K_i$ values (in nM) shown in Table 1 were determined using GraphPad Prism software.

TABLE 1

| | Receptor Binding, $K_i$ (nM) | | |
|---|---|---|---|
| Cpd | α1a-AR | α1b-AR | α1d-AR |
| 1 | 1.2 | 144 | 1.8 |
| 2 | 27.8 | 148 | 40.2 |
| 3 | 3 | 470 | 7.3 |
| 4 | 1.4 | 1385 | 88.6 |
| 5 | 3 | 470 | 7.3 |
| 6 | 1.4 | 1385 | 88.6 |
| 7 | 0.91 | 141 | 2 |
| 8 | 10.8 | 133 | 33.6 |
| 9 | 1.3 | 82 | 2.6 |
| 10 | 4.5 | 305 | 47 |
| 11 | 1.8 | 107 | 2.1 |
| 12 | 3.8 | 337 | 32 |
| 13 | 4 | 92 | 3 |
| 14 | 2.2 | 90.6 | 26 |
| 15 | 79 | 839 | 6.1 |
| 16 | 30.4 | 411 | 2.4 |
| 17 | 6.2 | 216 | 1.5 |
| 18 | 10.4 | 703 | 35.9 |
| 19 | 5.8 | 181 | 0.97 |
| 20 | 4.7 | 786 | 43.9 |
| 21 | 15.6 | 275 | 13 |
| 22 | 14 | 340 | 57 |
| 23 | 7 | 261 | 5.9 |

TABLE 1-continued

| | Receptor Binding, $K_i$ (nM) | | |
|---|---|---|---|
| Cpd | α1a-AR | α1b-AR | α1d-AR |
| 24 | 12 | 355 | 70 |
| 25 | 5.4 | 76 | 2.7 |
| 26 | 37.5 | 302 | 85.7 |
| 27 | 10.9 | 354 | 8.8 |
| 28 | 68.8 | 4403 | 48.6 |
| 29 | 12 | 300 | 4.1 |
| 30 | 30.5 | 681 | 86 |
| 31 | 16 | 690 | 12.4 |
| 32 | 23 | 639 | 60 |
| 33 | 3.3 | 299 | 1.6 |
| 34 | 43 | 1487 | 53 |

In Vivo Models

The ability of a test compound to relax prostatic smooth muscle tissue in vivo is evaluated using the prostatic intraurethral pressure (IUP) and blood pressure (MAP) in the anesthetized canine model. Alternatively, the ability of a test compound to relax prostate smooth muscle tissue in vivo is evaluated by evaluating the prostatic intraurethral pressure (IUP) and blood pressure (MAP) in the conscious canine model.

It is to be understood that the preceding description teaches the principles of the present invention, with examples thereof, which have emphasized certain aspects. It will also be understood that the practice of the invention encompasses all of the usual variations, adaptations and modifications as come within the scope of the following claims and their equivalents. However, numerous other equivalents not specifically elaborated on or discussed may nevertheless fall within the spirit and scope of the present invention and claims and are intended to be included.

Throughout this application, various publications are cited. The disclosure of all publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats.

What is claimed is:

1. A compound or the pharmaceutically acceptable salts, hydrates, stereoisomers, crystalline or amorphous forms thereof selected from the group consisting of:

N-cis-{4-[4-(2-isopropoxy-phenyl)-piperidin-1-yl]-cyclohexyl}-3,4-dimethoxy-benzenesulfonamide, 3,4-difluoro-N-cis-{4-[4-(2-isopropoxy-phenyl)-piperidin-1-yl]-cyclohexyl}-benzenesulfonamide, 3,4-difluoro-N-trans-{4-[4-(2-isopropoxy-phenyl)-piperidin-1-yl]-cyclohexyl}-benzenesulfonamide, 3,4-dimethoxy-N-cis-(4-{4-[2-(2,2,2-trifluoro-ethoxy)-phenyl]-piperidin-1-yl}-cyclohexyl)-benzenesulfonamide, 3,4-dimethoxy-N-trans-(4-{4-[2-(2,2,2-trifluoro-ethoxy)-phenyl]-piperidin-1-yl}-cyclohexyl)-benzenesulfonamide, N-cis-{4-[4-(2-cyclopropoxy-phenyl)-piperidin-1-yl]-cyclohexyl}-3,4-dimethoxy-benzenesulfonamide, 5-chloro-N-cis-{4-[4-(2-cyclopropoxy-phenyl)-piperidin-1-yl]-cyclohexyl}-2-methoxy-benzenesulfonamide, 5-chloro-N-cis-{4-[4-(2-cyclopropoxy-phenyl)-piperidin-1-yl]-cyclohexyl}-2-fluoro-benzenesulfonamide, 2,3-dihydro-benzo [1,4]dioxine-6-sulfonic acid cis-(4-{4-[2-(2,2,2-trifluoro-ethoxy)-phenyl]-piperidin-1-yl}-cyclohexyl)-amide, 5-chloro-2-methoxy-N-cis-(4-{4-[2-(2,2,2-trifluoro-ethoxy)-phenyl]-piperidin-1-yl}-cyclohexyl)-benzenesulfonamide, 5-chloro-2-methoxy-N-trans-(4-{4-[2-(2,2,2-trifluoro-ethoxy)-phenyl]-piperidin-1-yl}-cyclohexyl)-benzenesulfonamide, 5-chloro-2-fluoro-N-cis-(4-{4-[2-(2,2,2-trifluoro-ethoxy)-phenyl]-piperidin-1-yl}-cyclohexyl)-benzenesulfonamide, 5-chloro-2-fluoro-N-trans-(4-{4-[2-(2,2,2-trifluoro-ethoxy)-phenyl]-piperidin-1-yl}-cyclohexyl)-benzenesulfonamide, 3-difluoromethoxy-N-cis-(4-{4-[2-(2,2,2-trifluoro-ethoxy)-phenyl]-piperidin-1-yl}-cyclohexyl)-benzenesulfonamide, N-cis-(4-{4-[2-(2-fluoro-ethoxy)-phenyl]-piperidin-1-yl}-cyclohexyl)-3,4-dimethoxy-benzenesulfonamide, N-trans-(4-{4-[2-(2-fluoro-ethoxy)-phenyl]-piperidin-1-yl}-cyclohexyl)-3,4-dimethoxy-benzenesulfonamide, N-cis-(4-{4-[2-(2,2-difluoro-ethoxy)-phenyl]-piperidin-1-yl}-cyclohexyl)-3,4-dimethoxy-benzenesulfonamide, N-cis-{4-[4-(4-fluoro-2-isopropoxy-phenyl)-piperidin-1-yl]-cyclohexyl}-3,4-dimethoxy-benzenesulfonamide, N-cis-{4-[4-(5-fluoro-2-isopropoxy-phenyl)-piperidin-1-yl]-cyclohexyl}-3,4-dimethoxy-benzenesulfonamide, and N-trans-{4-[4-(5-fluoro-2-isopropoxy-phenyl)-piperidin-1-yl]-cyclohexyl}-3,4-dimethoxy-benzenesulfonamide.

2. A pharmaceutical composition, comprising a therapeutically effective amount of a compound according to claim 1 and a pharmaceutically acceptable carrier.

3. A process for preparing a pharmaceutical composition, comprising the step of intimately mixing a compound according to claim 1 with a pharmaceutically acceptable carrier.

4. A method of treating lower urinary tract symptoms (LUTS) comprising administering to a patient in need of such treatment an effective amount of a compound as claimed in claim 1.

5. The method of claim 4, wherein the effective amount is in a range of from about 0.001 mg/kg to about 300 mg/kg of body weight per day.

6. A method of treating benign prostatic hyperplasia (BPH) comprising administering to a patient in need of such treatment an effective amount of a compound as claimed in claim 1.

7. The method of claim 6, wherein the effective amount is in a range of from about 0.001 mg/kg to about 300 mg/kg of body weight per day.

* * * * *